US008350125B2

(12) United States Patent
Tanaka et al.

(10) Patent No.: US 8,350,125 B2
(45) Date of Patent: Jan. 8, 2013

(54) METHOD FOR PRODUCING YELLOW FLOWER BY CONTROLLING FLAVONOID SYNTHETIC PATHWAY

(75) Inventors: Yoshikazu Tanaka, Shiga (JP); Eiichiro Ono, Shiga (JP); Noriko Nakamura, Kyoto (JP); Masako Mizutani, Kyoto (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 382 days.

(21) Appl. No.: 12/711,701

(22) Filed: Feb. 24, 2010

(65) Prior Publication Data

US 2010/0199384 A1    Aug. 5, 2010

Related U.S. Application Data

(62) Division of application No. 10/583,110, filed as application No. PCT/JP2004/019461 on Dec. 17, 2004, now Pat. No. 7,750,209.

(30) Foreign Application Priority Data

Dec. 17, 2003  (JP) ................................ 2003-420046

(51) Int. Cl.
*C12N 15/29* (2006.01)
*C12N 15/82* (2006.01)
*A01H 5/00* (2006.01)

(52) U.S. Cl. ..................... 800/298; 800/278; 435/320.1; 435/419; 536/23.6

(58) Field of Classification Search .................. None
See application file for complete search history.

(56) References Cited

FOREIGN PATENT DOCUMENTS

| EP | 1 001 028 A1 | 5/2000 |
|----|----|----|
| EP | 1652916 | 5/2003 |
| JP | 2003-289884 | 10/2003 |
| WO | WO 96-25500 | 8/1996 |
| WO | WO 00/49155 | 8/2000 |
| WO | WO 2004/018682 | 3/2004 |
| WO | WO 2005/017147 | 2/2005 |

OTHER PUBLICATIONS

Bowie et al, Science 247:1306-1310, 1990.*
McConnell et al, Nature 411 (6838):709-713, 2001.*
Ono et al (2006, PNAS 103(29):11075-11080).*
Ono et al., "Yellow flowers generated by expression of the aurone biosynthetic pathway," PNAS, Jul. 18, 2006, vol. 103, No. 29, pp. 11075-11080.
Database EMBL [Online], Oct. 4, 2003, "*Scutellaria baicalensis* UBGAT-I mRNA for UDP-glucuronate: baicalein 7-O-glucuronosyltransferase, complete cds," XP002411055, EBI accession No. EM_PRO:AB042277.
Database EMBL [Online], Nov. 8, 2005, "*Antirrhinum majus* AM4'CGT mRNA for UDP-glucose glucosyltransferase, complete cds," XP002411056, EBI accession No. EM_PRO:AB198665.
Database EMBL [Online], Nov. 8, 2005, "*Linaria vulgaris* L4'CGT mRNA for UDP-glucose glucosyltransferase, complete cds," XP002411057, EBI accession No. EM_PRO:AB198666.
European Search Report dated Jan. 10, 2007, issued in European Application No. 04807816.6.
Yamazaki et al., "Molecular Cloning and Biochemical Characterization of a Novel Anthocyanin 5-O-Glucosyltransferase by mRNA Differential Display for Plant Forms Regarding Anthocyanin," The Journal of Biological Chemistry, vol. 274, No. 11, Mar. 12, 1999, pp. 7405-7411, American Society for Biochemistry and Molecular Biology, Baltimore, MD.
Bowie et al., Science 247:1306-1310 (1990).
McConnell et al., Nature 411 (6838): 709-713, 2001.
International Search Report issued Mar. 22, 2005, in International Application No. PCT/JP2004/019461, Dec. 17, 2004.
Tanaka et al., "Metabolic Engineering to Modify Flower Color," Plant Cell Physiol. 39(11), pp. 1119-1126 (1998), Japanese Society of Plant Physiologists, Kyoto, Japan.
Forkmann et al., "Metabolic engineering and applications of flavonoids," Curr. Opin. Biotechnol. 12:155-160 (2001).
Harborne et al., "Comparative Biochemistry of Flavonoids—I. Distrubution of Chalcone and Aurone Pigments in Plants," Phytochemistry, 1966, vol. 5, pp. 111-115, Pergamon Press Ltd., England.
Saito, Biohorti 1, pp. 49-57, (1990) (in Japanese).
Forkmann et al., "Biosynthesis of Flavonoids," Comprehensive Natural Products Chemistry, vol. 1, 1999, pp. 713-748, Elsevier, Amsterdam.
Davies et al., "Flower Colour," Biotechnology of Ornamental Plants, 1997, pp. 259-294, CAB International, Wallingford, UK.
Itoh et al., "Excision of Transposable Elements from the Chalcone Isomerase and Dihydroflavonol 4-Reductase Genes May Contribute to the Variegation of the Yellow-Flowered Carnation (*Dianthus caryophyllus*)," Plant Cell Physiol. 43(5), pp. 578-585 (2002), Japanese Society of Plant Physiologists, Kyoto, Japan.
Plant Cell Physiol. vol. 4, Supplement (2003), s158.
Davies et al., "Production of yellow colour in flowers: redirection of flavonoid biosynthesis in *Petunia*," The Plant Journal (1998), 13(2), pp. 259-266, Blackwell Sciences, Oxford, England.
Nakayama et al., "Aureusidin Synthase: A Polyphenol Oxidase Homolog Responsible for Flower Coloration," Science, vol. 290, pp. 1163-1166, Nov. 10, 2000, American Association for the Advancement of Science, Washington, DC.
Marrs et al., "A glutathione S-transferase involved in vacuolar transfer encoded by the maize gene Bronze-2," Nature, vol. 375, pp. 397-400, Jun. 1, 1995, Nature Publishing Group, London, England.
Springob et al., "Recent advances in the biosynthesis and accumulation of anthocyanins," Natural Product Reports, vol. 20, pp. 288-303, 2003.
Li et al., "Phylogenetic Analysis of the UDP-glycosyltransferase Multigene Family of *Arabidopsis thaliana*," The Journal of Biological Chemistry, vol. 276, No. 6, Issue of Feb. 9, 2001, pp. 4338-4343, Journal of Biological Chemistry, American Society for Biochemistry and Molecular Biology, Baltimore MD.

(Continued)

*Primary Examiner* — Stuart F Baum
(74) *Attorney, Agent, or Firm* — Drinker Biddle & Reath LLP

(57) ABSTRACT

There is provided a gene coding for the amino acid sequence listed as SEQ ID NO: 2 or SEQ ID NO: 70, for example. Co-expression of the 4'CGT gene and AS gene in a plant lacking natural aurone synthesis ability is carried out to successfully accumulate aurones and alter the flower color to have a yellow tint. In addition to the expression of both genes, the flavonoid pigment synthesis pathway of the host plant itself is inhibited to obtain flowers with a more defined yellow color.

11 Claims, 3 Drawing Sheets

OTHER PUBLICATIONS

Office Action mailed Sep. 1, 2011 issued in Canadian Application No. 2,550,507.

Vogt et al., "Cloning and expression of a cDNA encoding betanidin 5-O-glucosyltransferase, a betanidin- and flavonoid-specific enzyme with high homology to inducible glucosyltransferases from the Solanaceae," The Plant Journal, (1999), vol. 19, No. 15, pp. 509-519.

Vogt, "Substrate specificity and sequence analysis define a polyithyletic origin of betanidin 5- and 6-O-glucosyltransferase from *Dorotheanthus bellidiformis*," Planta (2002) 214: pp. 492-495.

Fukuchi-Mizutani et al., "Biochemical and Molecular Characterization of a Novel UDP-Glucose: Anthocyanin 3'-O-Glucosyltransferase, a Key Enzyme for Blue Anthocyanin Biosynthesis, from Gentian," Plant Physiology, Jul. 2003, vol. 132, pp. 1652-1663, American Society of Plant Physiologists, Lancaster, PA.

Martin et al., "Molecular evidence for pre-Cretaceous angiosperm origins," Nature, vol. 339, May 4, 1989, pp. 46-48, The Nature Publishing Group, London, England.

Yamazaki et al., "Two flavonoid glucosyltransferases from *Petunia hybrida*: molecular cloning, biochemical properties and developmentally regulated expression," Plant Molecular Biology, vol. 48, pp. 401-411, 2002, Kluwer Academic, Dordrecht, Holland.

Vogt, "Substrate specificity and sequence analysis define a polyphyletic origin of betanidin 5- and 6-O-glucosyltransferase from *Dorotheanthus bellidiformis*," Planta (2002) 214: pp. 492-495.

Fukuchi-Mizutani et al., "Biochemical and Molecular Characterization of a Novel UDP-Glucose: Anthocyanin 3'-O-Glucosyltransferase, a Key Enzyme for Blue Anthocyanin Biosynthesis, from Gentian," Plant Physiology, Jul. 2003, vol. 132, pp. 1652-1663, American Society of Plant Physiologists, Lancaster, PA.

Guterman et al., "Rose Scent: Genomics Approach to Discovering Novel Floral Fragrance-Related Genes," The Plant Cell, vol. 14, 2325-2338, Oct. 2002, American Society of Plan Physiologists, Rockville, MD.

Hirotani et al., "Cloning and expression of UDP-glucose: flavonoid 7-O-glucosyltransferase from hairy root cultures of *Scutellaria baicalensis*," Planta (2000) vol. 210, pp. 1006-1013.

Sato et al., "Enzymatic formation of aurones in the extracts of yellow snapdragon flowers," Plant Science, vol. 160: 229-236 (2001).

Martin et al., "Molecular evidence for pre-Cretaceous angiosperm origins," Nature, vol. 339, May 4, 1989, pp. 46-48, The Nature Publishing Group, London, England.

Mitsuhara et al., "Efficient Promoter Cassettes for Enhanced Expression of Foreign Genes in Dicotyledonous and Monocotyledonous Plants," Plant Cell Physiology, 37(1): pp. 49-59 (1996).

van Engelen et al., "pBINPLUS: an improved plant transformation vector based on pBIN19," Transgenic Research 4, pp. 288-290 (1995), Kluwer Academic Publishers, Dordrecht, Holland.

Aida et al., "Modification of flower color in torenia (*Torenia fournieri* Lind.) by genetic transformation," Plant Science, 153 (2000) pp. 33-42, Elsevier.

Gong et al., "Cloning and molecular analysis of structural genes involved in anthocyanin biosynthesis and expressed in a forma-specific manner in *Perilla frutescens*," Plant Molecular Biology, vol. 35, pp. 915-927, 1997 Kluwer Academic Publishers, Holland.

Suzuki et al., "Flower color modification of *Torenia hybrida* by cosuppression of anthocyanin biosynthesis genes," Molecular Breeding, vol. 6, pp. 239-246, 2000, Kluwer Academic Publishers, Dordrecht, Holland.

\* cited by examiner

SEQUENCE LISTING

```
<160> NUMBER OF SEQ ID NOS: 70

<210> SEQ ID NO 1
<211> LENGTH: 1422
<212> TYPE: DNA
<213> ORGANISM: Artificial Sequence
<220> FEATURE:
<221> NAME/KEY: CDS
<222> LOCATION: (1)..(1371)
<220> FEATURE:
<223> OTHER INFORMATION: Description of Artificial Sequence: Synthetic
      nucleotide construct

<400> SEQUENCE: 1 atg gga gaa gaa tac aag aaa aca cac aca ata gtc ttt cac act tca        48
Met Gly Glu Glu Tyr Lys Lys Thr His Thr Ile Val Phe His Thr Ser
 1               5                  10                  15 gaa gaa cac ctc aac tct tca ata gcc ctt gca aag ttc ata acc aaa        96
Glu Glu His Leu Asn Ser Ser Ile Ala Leu Ala Lys Phe Ile Thr Lys
                20                  25                  30 cac cac tct tca atc tcc atc act atc atc agc act gcc ccc gcc gaa       144
His His Ser Ser Ile Ser Ile Thr Ile Ile Ser Thr Ala Pro Ala Glu
            35                  40                  45 tct tct gaa gtg gcc aaa att att aat aat ccg tca ata act tac cgc       192
Ser Ser Glu Val Ala Lys Ile Ile Asn Asn Pro Ser Ile Thr Tyr Arg
        50                  55                  60 ggc ctc acc gcg gta gcg ctc cct gaa aat ctc acc agt aac att aat       240
Gly Leu Thr Ala Val Ala Leu Pro Glu Asn Leu Thr Ser Asn Ile Asn
    65                  70                  75                  80 aaa aac ccc gtc gaa ctt ttc ttc gaa atc cct cgt cta caa aac gcc       288
Lys Asn Pro Val Glu Leu Phe Phe Glu Ile Pro Arg Leu Gln Asn Ala
                    85                  90                  95 aac ctt cga gag gct tta cta gat att tcg cga aaa tcc gat atc aaa       336
Asn Leu Arg Glu Ala Leu Leu Asp Ile Ser Arg Lys Ser Asp Ile Lys
                100                 105                 110 gca tta atc atc gat ttc ttc tgc aat gcg gca ttt gaa gta tcc acc       384
Ala Leu Ile Ile Asp Phe Phe Cys Asn Ala Ala Phe Glu Val Ser Thr
            115                 120                 125 agc atg aac ata ccc act tac ttc gac gtc agt ggc ggc gct ttt ctc       432
Ser Met Asn Ile Pro Thr Tyr Phe Asp Val Ser Gly Gly Ala Phe Leu
        130                 135                 140
```

```
ctc tgc acg ttt ctc cac cac ccg aca cta cac caa act gtt cgt gga      480
Leu Cys Thr Phe Leu His His Pro Thr Leu His Gln Thr Val Arg Gly
145                 150                 155                 160 gac att gcg gat ttg aac gat tct gtt gag atg ccc ggg ttc cca ttg      528
Asp Ile Ala Asp Leu Asn Asp Ser Val Glu Met Pro Gly Phe Pro Leu
                165                 170                 175 att cac tcc tct gat tta cca atg agt ttg ttt tat cgt aag act aat      576
Ile His Ser Ser Asp Leu Pro Met Ser Leu Phe Tyr Arg Lys Thr Asn
                180                 185                 190 gtt tac aaa cac ttt cta gac act tcc tta aac atg cgc aaa tcg agt      624
Val Tyr Lys His Phe Leu Asp Thr Ser Leu Asn Met Arg Lys Ser Ser
            195                 200                 205 ggg ata ctc gtg aac acg ttt gtt gcg ctc gag ttt cga gct aag gaa      672
Gly Ile Leu Val Asn Thr Phe Val Ala Leu Glu Phe Arg Ala Lys Glu
    210                 215                 220 gct ttg tcc aac ggt ttg tac ggt cca act ccg cct ctt tat tta ctt      720
Ala Leu Ser Asn Gly Leu Tyr Gly Pro Thr Pro Pro Leu Tyr Leu Leu
225                 230                 235                 240 tca cat aca att gcc gaa ccc cac gac act aaa gtg ttg gta aac caa      768
Ser His Thr Ile Ala Glu Pro His Asp Thr Lys Val Leu Val Asn Gln
                245                 250                 255 cac gaa tgc cta tca tgg ctt gat ttg cag cct agt aaa agc gtg att      816
His Glu Cys Leu Ser Trp Leu Asp Leu Gln Pro Ser Lys Ser Val Ile
                260                 265                 270 ttc ctt tgt ttc gga aga aga gga gcg ttc tca gca caa cag ttg aaa      864
Phe Leu Cys Phe Gly Arg Arg Gly Ala Phe Ser Ala Gln Gln Leu Lys
            275                 280                 285 gaa att gcg ata ggg ttg gag aag agt gga tgt cga ttt ctt tgg tta      912
Glu Ile Ala Ile Gly Leu Glu Lys Ser Gly Cys Arg Phe Leu Trp Leu
    290                 295                 300 gcc cgc att tca ccg gag atg gac tta aat gcg ctt ctg ccg gag ggt      960
Ala Arg Ile Ser Pro Glu Met Asp Leu Asn Ala Leu Leu Pro Glu Gly
305                 310                 315                 320 ttt cta tcg aga act aaa gga gta ggg ttt gtg aca aac aca tgg gtg     1008
Phe Leu Ser Arg Thr Lys Gly Val Gly Phe Val Thr Asn Thr Trp Val
                325                 330                 335 ccg caa aaa gag gtg ttg agt cat gat gca gtg ggg ggg ttt gtg act     1056
Pro Gln Lys Glu Val Leu Ser His Asp Ala Val Gly Gly Phe Val Thr
                340                 345                 350 cat tgc ggg tgg agt tcg gtt ctt gaa gcg ctg tcg ttc ggt gtc ccg     1104
His Cys Gly Trp Ser Ser Val Leu Glu Ala Leu Ser Phe Gly Val Pro
            355                 360                 365 atg att ggt tgg ccg ttg tac gca gag cag agg atc aat agg gtg ttc     1152
Met Ile Gly Trp Pro Leu Tyr Ala Glu Gln Arg Ile Asn Arg Val Phe
    370                 375                 380 atg gtg gag gaa ata aag gtg gcg ctg cca ttg gat gag gaa gat gga     1200
Met Val Glu Glu Ile Lys Val Ala Leu Pro Leu Asp Glu Glu Asp Gly
385                 390                 395                 400 ttt gtg acg gcg atg gag ttg gag aag cgc gtc agg gag ttg atg gag     1248
Phe Val Thr Ala Met Glu Leu Glu Lys Arg Val Arg Glu Leu Met Glu
                405                 410                 415 tcg gta aag ggg aaa gaa gtg aag cgc cgt gtg gcg gaa ttg aaa atc     1296
Ser Val Lys Gly Lys Glu Val Lys Arg Arg Val Ala Glu Leu Lys Ile
                420                 425                 430 tct aca aag gca gcc gtg agt aaa ggt gga tcg tcc ttg gct tct ttg     1344
Ser Thr Lys Ala Ala Val Ser Lys Gly Gly Ser Ser Leu Ala Ser Leu
            435                 440                 445 gag aag ttc atc aac tcg gtc act cgt taaagtttct tactcaatat           1391
Glu Lys Phe Ile Asn Ser Val Thr Arg
    450                 455
```
atggtacatc ggtttaacta ccaaattta t 1422

<210> SEQ ID NO 2
<211> LENGTH: 457
<212> TYPE: PRT
<213> ORGANISM: Artificial Sequence
<220> FEATURE:
<223> OTHER INFORMATION: Description of Artificial Sequence: Synthetic protein

<400> SEQUENCE: 2

```
Met Gly Glu Glu Tyr Lys Lys Thr His Thr Ile Val Phe His Thr Ser
 1               5                  10                  15

Glu Glu His Leu Asn Ser Ser Ile Ala Leu Ala Lys Phe Ile Thr Lys
             20                  25                  30

His His Ser Ser Ile Ser Thr Ile Ile Ser Thr Ala Pro Ala Glu
         35                  40                  45

Ser Ser Glu Val Ala Lys Ile Ile Asn Asn Pro Ser Ile Thr Tyr Arg
     50                  55                  60

Gly Leu Thr Ala Val Ala Leu Pro Glu Asn Leu Thr Ser Asn Ile Asn
 65                  70                  75                  80

Lys Asn Pro Val Glu Leu Phe Phe Glu Ile Pro Arg Leu Gln Asn Ala
                 85                  90                  95

Asn Leu Arg Glu Ala Leu Leu Asp Ile Ser Arg Lys Ser Asp Ile Lys
            100                 105                 110

Ala Leu Ile Ile Asp Phe Phe Cys Asn Ala Ala Phe Glu Val Ser Thr
        115                 120                 125

Ser Met Asn Ile Pro Thr Tyr Phe Asp Val Ser Gly Gly Ala Phe Leu
    130                 135                 140

Leu Cys Thr Phe Leu His His Pro Thr Leu His Gln Thr Val Arg Gly
145                 150                 155                 160

Asp Ile Ala Asp Leu Asn Asp Ser Val Glu Met Pro Gly Phe Pro Leu
                165                 170                 175

Ile His Ser Ser Asp Leu Pro Met Ser Leu Phe Tyr Arg Lys Thr Asn
            180                 185                 190

Val Tyr Lys His Phe Leu Asp Thr Ser Leu Asn Met Arg Lys Ser Ser
        195                 200                 205

Gly Ile Leu Val Asn Thr Phe Val Ala Leu Glu Phe Arg Ala Lys Glu
    210                 215                 220

Ala Leu Ser Asn Gly Leu Tyr Gly Pro Thr Pro Leu Tyr Leu Leu
225                 230                 235                 240

Ser His Thr Ile Ala Glu Pro His Asp Thr Lys Val Leu Val Asn Gln
                245                 250                 255

His Glu Cys Leu Ser Trp Leu Asp Leu Gln Pro Ser Lys Ser Val Ile
            260                 265                 270

Phe Leu Cys Phe Gly Arg Arg Gly Ala Phe Ser Ala Gln Gln Leu Lys
        275                 280                 285

Glu Ile Ala Ile Gly Leu Glu Lys Ser Gly Cys Arg Phe Leu Trp Leu
    290                 295                 300

Ala Arg Ile Ser Pro Glu Met Asp Leu Asn Ala Leu Leu Pro Glu Gly
305                 310                 315                 320

Phe Leu Ser Arg Thr Lys Gly Val Gly Phe Val Thr Asn Thr Trp Val
                325                 330                 335

Pro Gln Lys Glu Val Leu Ser His Asp Ala Val Gly Gly Phe Val Thr
            340                 345                 350

His Cys Gly Trp Ser Ser Val Leu Glu Ala Leu Ser Phe Gly Val Pro
```

```
                    355                 360                 365

Met Ile Gly Trp Pro Leu Tyr Ala Glu Gln Arg Ile Asn Arg Val Phe
    370                 375                 380

Met Val Glu Glu Ile Lys Val Ala Leu Pro Leu Asp Glu Glu Asp Gly
385                 390                 395                 400

Phe Val Thr Ala Met Glu Leu Glu Lys Arg Val Arg Glu Leu Met Glu
                405                 410                 415

Ser Val Lys Gly Lys Glu Val Lys Arg Val Ala Glu Leu Lys Ile
                420                 425                 430

Ser Thr Lys Ala Ala Val Ser Lys Gly Gly Ser Ser Leu Ala Ser Leu
                435                 440                 445

Glu Lys Phe Ile Asn Ser Val Thr Arg
    450                 455

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaaatggtcg gattggctgg g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acctccaccc caactttcag g                                              21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgcataat ttggctagaa aagc                                           24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaatttgcc aaacactttc c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 7
tgcctcgaat ggttgagcac g                                             21

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctctcactct cacacccg                                                 18

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacgaatgct tagcatggct c                                             21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttattgccc actgaaaccc c                                             21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtctgaatt ggcttgattc c                                             21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aacccacaga aacccctgtt c                                             21

<210> SEQ ID NO 13
<211> LENGTH: 1446
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 13

```
atgggaaaac ttcacattgc cttatttcca gttatggctc atggtcacat gatcccaatg    60
ttggacatgg ccaagctctt tacctcaaga ggcatacaaa caacaatcat ttcgactctc   120
gccttcgctg atccgataaa caaagctcgt gattcgggcc tcgatattgg actaagcatc   180
ctcaaattcc caccagaagg atcaggaata ccagatcaca tggtgagcct tgatctagtt   240
actgaagatt ggctcccaaa gtttgttgag tcattagtct tattacaaga gccagttgag   300
aagcttatcg aagaactaaa gctcgactgt ctcgtttccg acatgttctt gccttggaca   360
gtcgattgtg cggctaagtt cggtattccg aggttggttt tccacggaac gagcaacttt   420
gcgttgtgtg cttcggagca aatgaagctt cacaagcctt ataagaatgt aacttctgat   480
actgagacat tgttatacc ggatttcccg catgagctga gtttgtgag gactcaagtg    540 gctccgtttc agcttgcgga aacggagaat ggattctcaa agttgatgaa acagatgacg   600
gagtctgttg gtagaagcta cggtgttgtg gttaacagtt tttatgagct cgagtcgact   660
tatgtggatt attacagaga ggttttgggt agaaagtctt ggaatatagg gcctctgttg   720
ttatccaaca atggcaatga ggaaaaagta caaggggaa aggaatctgc gattggcgaa    780
cacgaatgct tggcttggtt gaattccaag aagcagaatt cggttgttta cgtttgtttt   840
ggaagtatgg cgacttttac tccagcgcag ttgcgcgaaa ctgcgattgg actcgaggaa   900
tcaggccaag agttcatttg gtagttaaa aggccaaaa cgaagaaga aggaaaagga    960 aaagaagaat ggctgccaga aaattttgag gaaagagtga agatagagg cttgatcata    1020 agaggatggg cgccgcaatt gttgatactc gatcatcctg cggtaggagc tttcgtgacg   1080
cattgtggat ggaattcgac gttggaagga atatgcgccg gtgtgcctat ggtgacttgg   1140
ccagttttcg cagagcagtt tttcaatgag aagtttgtga cagaggtttt ggggaccggt   1200
gtttcggttg gaataagaa gtggctaagg gcagcaagtg aaggtgtgtc gagggaggca    1260
gtgacgaacg cggtgcagcg tgttatggtg ggagaaaatg cgtcggagat gagaaagcga   1320
gcgaagtatt ataaggaaat ggcgaggcgg gcggttgagg aaggcggttc gtcttataat   1380
ggtttgaatg agatgataga ggatttgagt gtgtaccgtg ctccagaaaa acaagactta   1440
aactag                                                              1446
```

<210> SEQ ID NO 14
<211> LENGTH: 1488
<212> TYPE: DNA
<213> ORGANISM: Artificial Sequence
<220> FEATURE:
<223> OTHER INFORMATION: Description of Artificial Sequence: Synthetic nucleotide construct

<400> SEQUENCE: 14

```
atggcctttc aaattcaacc agagcttcta aacttcgttt tcataccatt catggcccct    60
ggccactcaa tccctatgat agacttagcc aaattattcg cggaacgcgg cgtcaacgta   120
acgatcatcg taacacctct taacgccgca cgattcaatt ccgttattaa tcgagccgtt   180
gaatcaggac agtccattcg tcttctccaa gtaaaattcc ctggtgaaga agccgggttg   240
ccacctggat gcgaaagcgc cgagacttta ccatcttatg aattgattcc aaatttttt    300 accgccgtaa aaatgttaca caaccaatc gaggaagaat tgagaaattt gatccctta    360 ccaagctgcg tcatttgtga taaacacata ccctggactg ctcaaacgtg caagaatctc   420
cgaattccga ggtaattttt cgatggaatg agctgttttg ctcctttagt aacacacgtt   480
ctctacgtgt ctaaggttca tgaaaccgtt cctccaaacg agccgttcgt tgttcctgat   540
```

```
ttccccgatg agatagagtt aacgaggttt caattgccag ggttgttgaa tccaagtcca      600
aggataaatt tttacgattt tcgcgaacaa gtgaagaaaa ctgaggagga ggcttatggg      660
gtggtggtga acagttttga ggagctggaa aaagattatt tcgagatgtt tcggaaattg      720 aaaggggta aagtttggtg tgttgggcct ttgtcgcttt atggtaacga cgatttggac       780
agggctggaa gagggaataa ggcgtcgatt gatacggatc ggtgtatgaa atggcttgat      840
gatatgaaac cagaatctgt aatttatgcc tgtttgggaa gcctgagtcg tttgtcgcgt      900
tcacagttcg tcgaacttgc tttgggattg gaagcatcaa acactcgtt tgttctagtt       960 gttaaaaccg aaggagagaa gtcgttgaaa atagagaaat ggattttgga caatggattc     1020
gaggaaagaa cgaaagatag agggttcttg attcgtggtt ggtcgccaca agtgttgatc     1080
ttgtcgcatt ttgcagtggg aggattcttg acgcattgtg gttggaattc gacgcttgag     1140
ggcatttgtg ctggtttgcc aatggtgatg tggccgatgt tcggcgaaca gtttttgaat     1200
gagaagttag tggtgcagat tttggggacg ggtgtgggag ttggagcgaa aagtacggta     1260 catttgggggg atgaagagat ggatgagatg agagtgacga ggaagggat taccaaggcg     1320 gtcgtggcag ttatggatag aggaactgaa gggtgtgaga ggcggagaaa ggcgaaggag     1380
cttggtgaaa tggctaagag ggcagtccaa gttgggggat cttcatgtaa gaatgtcgac     1440
cagctaattc aagaagttgc accattgagt gtagcgaggg atgtgtaa                  1488
```

<210> SEQ ID NO 15
<211> LENGTH: 1446
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 15

```
atgggttctc tccctgaaaa tgagctcaac aaaccacatg ctgtgtgcat accctatcca       60
gcactagggc atttcagtcc catgctagat tttgctaagc tcctccacca aaaaggcttt      120
cacataacct tcgtcaacac cgagtacatc cgtctccgcc tcctcaagtc ctgtggccct      180
gccgccctgg acgggctacc ggactttcgc ttcatgacta tccccgatgg cctccctttg      240
tcggacgacg tttcgcgtga tgtcgcttcc atttctgtct ctactaacaa aacttgctta      300 gaacccttttt gtgaggtgct atcggacctc atggataatg gttccaaccc gccggtgagc      360
tgcattgtgt ccgacggggt aatgagtttc acccttgagg cggcggagag gtttggactg      420
ccagaggtgc tgttctggac gcccgctgct tgtggcatct tagctttcac gcagtataag      480
catcttgtgg agagaggata tgtacctctc aaagatacga gccaggtaac aaatggctac      540
ctggaaacaa tattagattg ggttccaggg atgaaggata ttcgattgag ggaattccca      600
actttcataa gaacgacgga cccaaacgac gttatgctgg atttttctaat aaaacaagtt     660 gacgccaccc cgaaagccaa tgctgtgatc atcaacacgt tcgacacatt ggaaagtgac      720
gctctcaacg ccctctctgt catgtttccg cgcatataca cactcgggcc tctccatatg     780
atgttgaata atcccgaggt cgacgaaccc tctaatgcaa tcaaatttaa tctttggaaa     840
gaagactcac attgcctaga ttggctcgat gtgaacgagc ccggatcagt tgtatacgtg     900
aattttggca gctcaacaat tctgactgtt gaacaactaa ctgaattagc atggggcctt     960
gctaacagca agaaaccgtt cctttggatc atcaggcctg atttagtaac tggtgcatcc    1020
tccatgcttc cgcctgagtt cctggtcgag actaaagaca gaagcatgtt agtgagttgg    1080
tgcaaccaag aacaagtgtt gaagcacccc gcgactggag tgttcttgac gcattgtgga    1140
```

```
tggaattcga cgattgaaag catttgcagc ggcgtgccaa tgatttgttg gccttactac    1200
gctgagcagc aaaccaactg taggtacagt tgtgtggaat gggaaatagg aatggagatc    1260
attgacaacg atgtgaagag agatgaggtg gaattgctgg tgattaagtt gatggatggt    1320
atcaagggaa agaaaatgaa aagaaagct atggagtgga agaggaaagc agaagaggcg     1380
gtagcttttg ggggctcttc ctacatgaat ttggataaac ttattagcga cgtgcttttt    1440
ccataa                                                                1446
```

<210> SEQ ID NO 16
<211> LENGTH: 1458
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 16

```
atggcaggtc caaattgcaa gcctcacgcc atcatgatcg cacttcctta ccaaggccac    60
ataactcctt ttgtcaatct tgcactaaaa cttgcttcca atggctttac aatcactttt    120
gttcaccttg aatttatcca ccaaatgttg tctaaagccc ataacgccac taaaactgaa    180
gcagatttat tttcggaagc acgagaatcc ggtctcgaca tacgttacac aacgattgac    240
gatggttttc ctttggaatt cgacagggct ctccactccg aggagtattg gcactccatg    300
ttgcgagatt tcccgttaca cgtcgatgag tttgttcgaa aagtcgtgga gtcagagcca    360
tttttagagc acttttttgg tacggatact atgtatacat ggcctgcaac cattgcaaag    420
aaacataatc ttgtgaatat tcgttttggg actgaaccag ccctggtgtt ttctttgtct    480
taccatataa accttctgaa gcaaaatggt cattttccat gtaaagaaaa tattgatgag    540
gaaataaatt acgtaccagg agttgattca ataagtacaa gggatttaat gtcttatttt    600
aaagaaccag gatcagaaac attagagaaa atgttgtgc tcaaggcatt tgaaggagtg     660
aagaaagctg atttcatctt gcataacaca ttgcaagaac tagaatctga cacactctca    720
gctcttacca aaatgcagcc aaattacgcc gttggaccta taatttctc caaacatact     780 cctaaaactg tcaccaagag tctacggtct gaattcgact gcaccaactg gctcgactct    840
aagcctccca actctatttt atacgtctcg tttggtagtt ttattcagac aagcaaagag    900
gtaattgaag aaatcgctta cggtcttctc cttagtgaag ttaactttat atgggtggtt    960
agaacagata gtgtgagttt agaggataac gaggttttgc cggttggatt tagggatgag    1020
gttaaagata gggggttgat agttccgtgg tgtgatcaaa ttacggtttt gtctaatcgc    1080
gcggttggag gattcttgac gcattgtgga tggaactcgg tattagagag tatgtggtgt    1140
ggcgttccta tgatttgtta tccgttaaca tatgatcaac ctactaatag gaaactattg    1200
gttgatgatt ggaagattgg cattaatctt gcgacggag cgttgattaa tagaaaagaa     1260
attgcagaga agattaaggc cttgatgagt gaaagtactt cagaggggtt gagggaagaa    1320
tctgagaaag ttaagggctt gttgaagaat gcactggaag ttggtggttc atcagagaag    1380
aatttcaata aatttattga ggatttgaag gcaaaaattc aaataatgaa agagcaaatg    1440
cctgctaata ccagttga                                                  1458
```

<210> SEQ ID NO 17
<211> LENGTH: 1443
<212> TYPE: DNA
<213> ORGANISM: Artificial Sequence
<220> FEATURE:

<223> OTHER INFORMATION: Description of Artificial Sequence: Synthetic
     nucleotide construct

<400> SEQUENCE: 17

```
atgggttcca cagccgaaaa taaacagaaa acccacattg tgtgcatacc ctacccagcc      60
caggggcaca tcagccccat gctaaagtta gccaaactgc tacaccaaaa cggcttttac     120
atcacttttg tcaacacgga gtacaaccac cgccgcctca tcaagtcccg cggccccacc     180
gccctcgacg gattgcccga tttccggttc gttacgatcc ccgacgggct tcctttctct     240
gaagccgacg ccacacagga tatcccttct ctttgtgttt caaccaccaa cacttgcttg     300
gagcccttt gcgagctgct gtcgaacctc aataactccg gcccggacgt gccccggtg      360
agctgcatcg tatccgatgg tgtcatgagc ttcacgttga aggcggcgga gagatttggg     420
ctgccggagg tgctgttctg gacgacgagt gcgtgtgggt tcttggcgta tacgcagtat     480
aagcatctcg tggagaaagg ctatgtaccc ctcaaagata tgagccaagt aacggatgga     540
tatttgaaaa caagcatgga ctggattcca ggaacgaagg acatccaact aagggacttc     600
ccctctttca tcaggacaac agatccagaa gacatcatgc ttaattttt aatacaagaa     660
actgatgttg ttccgagagc caaagctgta ataatcaaca ccttcgacat gttagaacac     720
gacgtcctgg aagcgctctc caccatgttt tcacgcgttt acagcatcgg ccctcttcag     780
ctgatgatga attatgttca caacgagtcc cttaaatcca tcagttccag tctatggaaa     840
gaagaaacac attgcgtcga ttggctcgat tcaaggagc ccgaatccgt tgtgtacgta      900
aattttggca gcataactgt cgtgactgca gaacaactga ctgagtttgc gtgggggctc     960
gctaatagta agaagacttt cctatgggtt attaggcctg atatagttgc tggagactcg    1020
gctatgctgc cccctgaatt cgtgacgggg acaaaagata gaagcatgtt aatcagctgg    1080
tgtaaccaag aacaggtgtt gaatcaccca tcaattggag ggttttttgac gcacagtggt    1140
tggaattcga cgattgaaag tatagtcgag ggagttcctg tgatttgctg gccttttcttt    1200
gctgagcagc aaacaaattg taggttcagt tgcgtggaat gggaaatagg aatggagatt    1260
gataataatg tgaagagaga tgaggttgaa gttttggtga gggaattgat ggatggagag    1320
aggggggaaga aaatgaagga gaaagctatg gagtggaaag ggaaagcatt agaggcaact    1380
gcacttgggg gctcttccta cttgaacttg gaaaaactaa ttaaggaggt gcttttgcat    1440
taa                                                                  1443
```

<210> SEQ ID NO 18
<211> LENGTH: 1407
<212> TYPE: DNA
<213> ORGANISM: Artificial Sequence
<220> FEATURE:
<223> OTHER INFORMATION: Description of Artificial Sequence: Synthetic
     nucleotide construct

<400> SEQUENCE: 18

```
atggcatctt ctccccataa ccagccaacc acgccccgcc acgtggtggc cctaccctac      60
cccggccgcg gccacataaa ccccatgctc aacatctgca agccgtagc ggagaagagc     120
agccacatca acataacaat catcctaacc gaggaatggc tcggcttaat cggctcagcc     180
gacaagccgc cgaacataag ctacgccgcg ataccgaaca ttctgccgtc ggagcacgtt     240
cgcggcgagg atccacatgg ttttgggcg gctgtttggc agaagatgga ggagccggtt     300
gatcggctgc tggacgagct tcggcttaat aataacaagc cggagtttgt gatagccgat     360
gctttcttgc attgggcggc tgacgtggcg ggcaggagga atattcccctt ggcatctgtt     420
```

```
tggccaatgt cggcgtccac gttcacggtg ctttaccact ttgaccttct cgttgaccac    480
ggacactttc cgatcgacat accagtgaat ggagatgcta ttgtggatta catcccggga    540
ctccctccag ttcgcgtcgc agattttcca aaagacataa gaaaacaaga agacgcatcc    600
ttcgtcctta aactcattcc caactcacca aaattcatca tcttcacttc aatttacgac    660
ctcgaatcca agatcatcga cgctctaaag caaaaatctt ccttctcaat ctacaacatt    720
ggtcctcatg cttcctattc caaactcaaa cacatcctca actcggataa aatcacgaaa    780
cctgatcaag ataaccccga ctacttaaaa tggttagatc tccaacctcc caactccgtc    840
ttgtacattt cactcggcag tttcctatcc atttccgcag cccaaatgga tgaactcgca    900
accggaatac gaaactctgg tgtccgcttt tgtgggtgg cacgtggcga aacaaaccgg    960
ttgaaagaga tttgttgtga tcatgaaaag gggctgatca tagaatggtg cgatcaaatg   1020
caggttcttt ctcattcttc ggttggtgga ttcttgtcgc attgtggttg gaattcgact   1080
aaagaggcgt tgatggccgg ggtgccgttt ttgactattc caattatgtt tgatcaagtg   1140
tctaacgcga aggcggtcgt ggaagattgg agggtgggg ggagggtggt gaatgagttt   1200
aatgaagaag agttggtggg aggagatgag attgcgaata ttgtgaggag gtttatggat   1260
atggaaaatg gtgagaggaa agagttgacg aaaaatgtga agaggtgca gaagatttgt   1320 gcgagagagt tcgaagatgg agatggacag tcgtttgagt ttaatgttga aagtttggtt   1380
caattgattc tgcaattggg tccgtaa                                      1407
```

<210> SEQ ID NO 19
<211> LENGTH: 1428
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 19

```
atgaacaaca caacccaaca acaaacagta gcattagcac tagcacctca ctgtttaatc     60
gtcccattcc cattccaagg ccacattaac cccttactcc aattcgccaa acgcctcata    120
actcaccaca acaaaaacct ccaaatcaca ttcgcactca ccaaattcat cctcaccaac    180
ctctcctccg gtgccggaga atcatccttc tctctccggt caatctccga cggcttcgac    240
gccggcggcc gcgctcaggc caactccggc gccgaatacc tctccaaatt ccgcgagatc    300
ggatctcaaa ccctaaccga acttatccaa gacctatccg aatcgggtcg acccgttgac    360
tgcgtggtct acgacccgtt cgtaccttgg gccttagatg ttgccaaggg taaattcgga    420
atttcaacgg cggcgttttt tacgcagtcg tgtgcggtgg ataatatata cagtcgggtt    480
tataacggcg atttggagct gccgttgccg gagaatgagg tggttagggt tccgggtttg    540
ccggagatgg agccgtttga gatgccgagc tttgtgtatt taaacgggtc gtacccgtcg    600
agttttgaga tggttgtggg tcagtttagg aatgttgatg aggcggattg ggttttttgtc    660 aacactttt atgagttgga gaaagaggtc attgactgga tgtcaaaatc ttggcgagtg    720
aaagcaattg gacctaccat accatcaatg ttcatggaca agagattgca agaggacaaa    780
tcatacggtc ttagcatgtt caagcataca acaaatgact gcataaattg gctcaacgga    840
aaacaatcaa aatccgtcat ttatgtcgca tttggaagtc ttgcagaatt atcccacgac    900
caaactcaag aactggcaca cgccttaaca acctacgaca aacacttctt atgggttgta    960
cgatcatcga agaagctaa gcttcccaa aattttgcta cgaaacatc taagaaaggg   1020 ttgatagtgt cgtggtgccc tcaattagag gtcttgtcgc acgaggccat cggttgtttc   1080
```

```
gtgactcatt gtggttggaa ttcaacgctc gagggattga gtttgggggt gcctatggtg    1140
gcgatgccac agtggacgga tcagagtacg aacgctaagt ttatcgtgga tgtttggggt    1200
gtgggtgttc gggctaaggt ggacgagggg ggattagcga ggcaagatga gatagttcgt    1260
tgcttaggga gcgtcatgga aggggagaac ggagaaaaga taagaaagaa tgcgaatgaa    1320
tggaaggaac gggcgtgcaa tgcagttgat gaaggggga gttcagacaa aaatattgaa    1380
gaatttgtta ctacgttgat aagttcccat gacttgcgtc aagagtaa               1428
```

<210> SEQ ID NO 20
<211> LENGTH: 1425
<212> TYPE: DNA
<213> ORGANISM: Artificial Sequence
<220> FEATURE:
<223> OTHER INFORMATION: Description of Artificial Sequence: Synthetic
      nucleotide construct
<220> FEATURE:
<221> NAME/KEY: modified_base
<222> LOCATION: (1349)
<223> OTHER INFORMATION: a, t, c, g, unknown or other

<400> SEQUENCE: 20

```
atgtctagtg agagccaaat aaacttagtg ttcatccctc tccctgtaaa gggacacatt     60
gtctcaacgc tagagacggc aaagctactc gtcgatcgaa acaaacgcct caccatcaca    120
atcctcctca tgaagctgcc agtcgacgcc aaggtagatg attccttcac aaaaaatccc    180
tcctgctctc aaataacttt tgtacatctc cctcgaatcg agcacagttc catgaaacca    240
ccgggaactc ccgaatcctt tgtacacagg ttcgtcgaga gccaaaaatg tctcgtaaga    300
gatgcggtgg ttaaagcaac ggagggctca aaatcaaaca ggctagccgg atttgtaatc    360
gacatgttct gcaccccgat gattgatgtg gccaatgaat ttggcgtccc gacatacgtg    420
gctttcacgt ccggggccgc aactctcggg ctattgttcc atttgcagag tcttagagat    480
gaatttaatc aggacgtgaa ggagtacgag aactcggaag ttgagatatc gatcccggct    540
tatgttaacc cgttcccttc caaatccttg ccgtctcctg tcttcaacga ggacggtgtt    600
tttcttagtc ttgcaaaggg gttcagagag ctaaaggta tattgatcaa caccttttta    660
gaatttgaat cccatgccat taaatcgctc tccaacgatg cgagaatccc gcctgtttac    720
cccatcgggc cagtaattca cgccacggaa gataatgcaa acaaaggaaa gcaggacgaa    780
atcatcgcgt ggcttgacga gcaacctgat tcatccgtcg tgtttctttg cttcggaagc    840
gctggatgct ttgaagaaaa tcaagtgaag gagattgcag tggcgctcga caaaagtgga    900
taccggtttt tatggtcatt gagaaagccg cctcccaaag aaaaagcgga gtttccaggg    960
gagtacaaag attttaatga agttttacca gaagggttct acaacgtac gtccgggaga   1020 ggtaaggtaa taggatgggc tccgcagatg gccgtgttgt ctcacaatgc ggtgggagga   1080
ttcgtgtcgc attgcggctg gaactcgacg ttggagagtg tttggtgcgg agtgccaatg   1140
gccgtgtggc cattggcggc cgagcaacat gcgaacgcgt tccagttggt gaaggagttg   1200
ggaattgcgg tggagattaa gatggattat aggaagaaca gtggtgtgat tgtgaggca   1260 aaaatgattg agaaaggaat cagggagttg atggaccccgg aaaatgagat aagggtaat   1320 gtgaaagtga tgaaaaagga gagtaggana gctgtcgtgg atggtgggac ttctttgat   1380 tacttggatc gttttgttga aactgtcgtg aataatgttt tgtga                  1425
```

<210> SEQ ID NO 21
<211> LENGTH: 1446
<212> TYPE: DNA

```
<213> ORGANISM: Artificial Sequence
<220> FEATURE:
<223> OTHER INFORMATION: Description of Artificial Sequence: Synthetic
      nucleotide construct

<400> SEQUENCE: 21
atgggttccg tagccggaaa cagttacaaa cggcctcatg ctgtgtgcat acccttcccg      60
gcgcaggggc acatcaaccc catgctgaag ttggccaaac tcctccacca aaagggcttc     120
cacatcacat tcgtcaacac agagtacaac caccgccgct tgctcaagtc cctcggcccc     180
gacgctctcg atggcttgcc ggatttccga ttcgcaacca tccccgacgg tcttcctccg     240
tctgacgcgg acgtcactca ggatgttcct tctctttgta tgtccaccac taacacttgc     300
ttggagccct ttaccgagtt gctgttgaaa ctcaataact ccggcccgga cgtgccaccg     360
gtgacctgca tcgtctcgga tggtgtcatg agcttcacat tgaaggcggc ggagaggttt     420
gcgctgccgg aagtgctgtt ctggacgacg agtgcgtgtg gtttcttggc gtacacgcag     480
tataagcgtc tcttggagaa aggctatgtc cctctcaaag atatgagcca gttaacaaat     540
agctatctgg aaacaaccct cgactgggtt ccaggaatga aggatatccg attaagggac     600
ttcccatcat tcatcaggac aacggatcca aaagacatca tgtacaattt cgtattacaa     660
gaaaccgacg ctgtctccag agccaaagct ctgatcatca acacctttca tacattggaa     720
cacgacgttg taaatgccct ctccaccatg tttccacgtg tttacaccat cggctctctt     780
cagctgatgt tggaccaagt tcatgacaag agccttaacg ccatcaactc caatctctgg     840
aaagaagaat cgcaatgcat cgattggctc aattcaaaag agcccgaatc cgttgtgtat     900
gtgaatttcg gtagtgtcac tgttgtgact gctcaacaac tgacggaatt tgcgtggggg     960
cttgcgaaca gcaacaagac tttttttatgg gttattaggc ctgatatagt tgttggagac    1020
tcggcaatgc tgccccctga attcttgacg gacacggaag acagaagcat gctaataagc    1080
tggtgtaacc aagaacaggt gttgaggcac ccttccatcc gaggattttt gacgcacagt    1140
ggttggaact cgacgcttga agtattgtc agcggagtgc ctatgatatg ttggcctttc     1200
tttgctgagc aacagacaaa ttgtaggttc agttgcgtgg aatgggaaat aggaatggag    1260
attgacaata atgtgaagag agatgaggtt gaggtgctgg tgagagagtt gatggatggt    1320
gaaaagggga agaaaatgaa gaagaaagct atggagtgga agatgaaagc agaagcagca    1380 gctgccctg ggggaccttc gtctttaaat ttggaaaaac ttattgagga ggtgcttttg     1440
caataa                                                              1446

<210> SEQ ID NO 22
<211> LENGTH: 1308
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 22
atgaaggctc atgcagtgat gcttccttgc cccgtacaag ggcacttaaa tcctatgctg       60
aaactggcca aaatattgca ttcaagaggc ttcttcatca cattcgtgaa cacggaattc     120
aatcacaatc gtctagtgcg tgcgagaggc cccgaatctg ttaaaggtcg cgatgatttt     180
cagttcaaaa ccatacctga tggactaccg cctttgata aggacgcaac gcaagacata     240
cctcaactgt gtgattctct tcaaaagaat ggtcttcctc cattgttgga cctcattaaa     300
agtattaatg attcaccgga ctgtccaaat gttacctgta tagtgattga tttggccatg     360
```

```
agtttcgctc ttgatgcggc cgaggtgttc aaaattccca cggtgtactt ttcgccaact      420
agtgcttgtg gattcatggg gttttgcaat tatgaagagc ttgtgaatcg aggattgttt      480
ccacttaaag atgaaagtca aataactaat ggctatcttg ataccaaact agactgggtg      540
ccagggatga agaacattag gctcagagat tttcctagtt tcatccgaac gactgatcca      600
gatgatatca tggtgaactt catgattttt aacatgaaga atgcgcctcg tgcaaaggct      660
gtggtagtca acacattcga tgaattggag aaagatgtat tggaggccct aagtaaaaaa      720
tttgatcatg ttttttccat aggcccactc caattgatgg agaaggcttt ccaaaagcct      780
gaggtaaaat ctataggatc aagcttgtgg aaagaagaca cacgtgcat cgcctggctc       840 aacggcaggg agccaaattc tgtgttgtac gtgaactttg aagcatcac agtgttgtca       900 cctcaacaac tattggagtt cgcatggggc ctagccaata gcaaccatta ctttttgtgg      960
atcataaggc cagatttggt aagtggagaa tctgcgattt tatccgaaga gtactcaaag     1020
gaagttgaag gcgggcgat gatggtgcgt tggtgctctc aagagcaagt attggcccat      1080
ccttcggtag gtggattctt gacacattct ggctggaact cgactatcga aggaatgtca     1140
gaaggtgttc ctatgatttg ttggccttt tttgctgacc aacagaccaa ttgtcggtat      1200
gcatgcacgg agtgggagat tggaatggag attgaaggag aggttacgag ggataaagtg     1260
gcggatttgg tgaaaatatt gatggaggag ggaaggggag agcgatga                   1308

<210> SEQ ID NO 23
<211> LENGTH: 1506
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 23
atggccattc atgaacaaaa acctcacttt gtcctgttcc ctttcatggc acaaggccat       60
atgattccca tggtagatat cgccagatta ctcgcgaagc gcggtgtcac aatcaccatt      120
ctactcacac cccacaatgc caacagggtc aaaacagtca ttgctcgtgc aatcgattca      180
ggactaaata tcaatgtcat ccacttcaaa tttccatccg ttgaggtcgg attgcccgaa      240
ggttgtgaga atttcgatat gctccctgac atcaatggcg cattgcagtt tttcaaagcc      300
actttcatgt tacaagaaca ggtcgaagag ttgcttccaa agctcgagcc tcttccgagc      360
tgcctaattg ctgatatgtg ctttccatgg acaacaaatc ttgctttgaa gttaaatgtt      420
ccaagaattg tgtttcacgg gacaagttgc tttttctctcc tatgtatgca cgttttagga      480
acttctaagg atttcgaagg tgtgactaac gaaacggagt acttccttgt gcctggatta      540
ccagataaaa tcgaataac caaaattcag cttaggggca cccttattca atgaattca       600 gactggacga agtttcgtga tgaggtgcga gaggctgagg taaaagcatt tggaacggtg      660
gccaatactt ttgaagattt ggaaccagag tatgtcaaag aatacagcag agttaaaggc      720
aaaaaagtct ggtgcatagg tcctgtttca ttatgcaaca agatggcat agacaaggcc      780 gaaagaggta acatggcttc aatcgacgca caccattgct tgaagtggct caattcacac      840
gaacaaaagt ctgttatttta cgtctgcctt ggaagcatat ctcgcctcgc tacttcacaa      900
ctgatagagc ttggattggc tttagaagca tcaaacagac cttttatttg ggtagttaga      960
gatccatcac aagaacttaa aaaatggttt ttgaatgaga aatttgagga aagggtaaag     1020
gatagaggcc ttttgatcaa cggttgggcg cctcaagtgc tcatactttc ccatccatct     1080
gttggagggt ttgtaacgca ctgcggctgg aactcgatgc ttgaaggggt tacttcaggc     1140
```

```
ttgccgatga taacgtggcc tgtatttgct gagcagtttt gtaatgaaaa gtttattgtt      1200
cacgtgatca agactgggat aagagtgggt gttgaagtgc ctatcatctt tggagatgaa      1260
gaaaaagtcg gagttttggt gaagaatgat gagataaaga tggttataga taagttgatg      1320
gatggaggag aagagggaga agagagaaga gagagagctc aaaagcttgg agaaatggca      1380
aaaaaggcaa tggaggaggg tggttcttct tatcataatt tgacatcggt catgcaagat      1440
gtcatgatgc aacaagctaa taatggagat caatatgaag atggtgttac agttataaat      1500
acatga                                                                 1506
```

```
<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggggatcca tggctagtga gagccaaata                                        30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccctcgagg gtacctcaca aaacattatt cacgac                                 36

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atgggagaag aatacaagaa aaca                                              24

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
taaaatttgg tagttaaacc gatgta                                            26

<210> SEQ ID NO 28
<211> LENGTH: 1386
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 28
atgctgagcc tcgccaaaat tctgcaccaa aagggattcc atatcacttt cgttaacact      60
```

```
gaatttaacc atgaacgcct cctgagaacg agaggcccga attcccttga cgggttgcct    120
tcgtttcgat tcgagacaat tcccgacggt cttccgccat cagaccccga tgctacacaa    180
aacgttgcat tattgtttga gtccagcaca tccaaatgct tagctccatt cagggacctt    240
cttgctaagc taaaccacac cgacgtgccg ccagttactt gcatactatc cgacttaatc    300
atgagcttca ctcttgaagc tgctcaagag ctcagcatcc ctgatgtcct tttttggacc    360
gctagcgctt gtggatacct cgcttatgca cactatgcca cgcttattga aaaggattt    420 acacctttca agatacgag ttgcttgacc aatgggtatt tggataccgt tattgatgat    480
attcctagtc tggaaggcat acgtctgaga gacattccaa gttttatcag aacaactaat    540
ccagatgaca ttttgatgaa ctttgtgttg cgagaaacag agagagctag aaaaggttcc    600
gccgtaatct ttaacacgtt cgagtgcctc gaggttgaag cattaaacgt actttcatcc    660
atgttgcctc cagtttacac agttggaccc ctgcatttgg ttgaaaagca tgttggtcac    720
aaaggattgg aggtgcttgg atcaaattta tggaaagaag agccaaaatg tctcgaatgg    780
cttgactccc aaattcccaa ctcagtggtt tacgttaatt ttggaagcat cgctgtcatg    840
acaactgacc aactgattga gttttcttgg ggtcttgcta atagcaacat atccttcttg    900
tggattataa gacctgacct tgtctcaggg aaaacgctg ttcttccacc cgaatttctc    960
gaagccacaa agaaagagg gtgtttagca aattggtgcc ctcaagagaa agttcttagc   1020
cacccatcca tcagaggatt cttaactcac agcggatgga attcaactct tgagagcatt   1080
tgcagtggag ttccaatgat cagttggccg ttcttcgccg aacaacgac taactgttgg   1140 ttttgctgca caaatgggg cataggcata gagctagaca atgatgtcaa aagggataaa   1200
gtggaagacc ttgtgcgcga attgatgtct ggggataaag ggaaagagat tatgaaaatg   1260
gctatggagt ggaagaagct ggccgaagag tctgcccaga gttcatcttt taagaatcta   1320
gagaaagtga ttcatgaagt gcttttacca ccactacaag tgtgggatcc taaggattcc   1380
acctaa                                                              1386

<210> SEQ ID NO 29
<211> LENGTH: 1374
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 29
atggaggaca ctatcgttct ctacgcttca gcagagcacc ttaactccat gctactactc     60
ggcaaactca tcaacaaaca ccaccccaca atctccgtcg ccattatcag caccgcccca    120
aacgccgccg ctagttccgt cgccgacgtg gcggccatat cttatcagca actcaaaccg    180
gccactctcc cttcggatct aaccaaaaac ccaatcgagc tcttcttcga atcccacgt    240 ctacataatc ctaacttgct cgaagcgctg aagaactgt cactaaaatc aaaagtaagg    300
gcatttgtga tagatttctt ttgcaatccc gcatttgagg tttcgactag cttgaacata    360
cccacttact tctatgtcag cagcggcgcg tttgggctat cgggttctt gcattttccg    420 acaatcgacg aaactgtcga aaagacatc ggtgaactga cgatatctt ggagatcccg    480 ggttgccccc cggttttgtc ctcggatttt ccgaaggta tgttctttcg caagagtaac    540
acttacaagc attttttaga cacggcgaaa acatgagga gagcgaaagg gatcgtggtg    600
aacgccttcg acgcgatgga gttccgagct aaagaagccc tcgtcaacaa tctgtgcgta    660
cccaattcgc caactccccc agttttctta gtcggcccat tggtcggagc aagcacaact    720
```

```
acgaaaacca caaacgaaca gcacgaatgc ttgaaatggc tggacgtgca gccagacaga    780
agcgtgatct tcttatgttt cggtaggagg ggtttgttct ccgcagacca attgaaggaa    840
atcgcaattg gtctggagaa cagcggccac aggttcctgt ggtccgtgcg ttgcccacca    900
agtaagccta actcttataa cactgatccg gacctggacg agctcctgcc cgagggtttt    960
ttgtccagga ccgagacccg gggtttcgtg atcaagtcgt gggcgcctca gaaggaggtg   1020
ctgagccatg gcgcggttgg agggttcgtg acgcactgtg ggaggagttc gatattggaa   1080
gcggtgtcgt ttggggtgcc gatgatcggg tggccgatat acgcggagca gaggatgaat   1140
agggtgttca tggtggagga gatgaaggtg gcgttgcagt tggatgaggt ggaggaaggg   1200
ttcgtggcgg cggtggaatt ggagaagaga gtgaaggagt tgatggattc gaagaatggg   1260
agagcggtta ggcagagagt gaaggagatg aaagtggcgg ctgaggtggc ggttgaaaag   1320
ggtggttcgt cagttgtggc gttgcaacgc tttgttgata tggtggtttc ttaa         1374
```

<210> SEQ ID NO 30
<211> LENGTH: 1362
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 30

```
atggaggcag acaaagaaaa tctcaagatt ttaatgttcc catggttggc tcatggtcat     60
atatttccat ttcttgagct agccaaaaga atcttgaagc gaaaaaactg gcacatatac    120
ttgtgtacca cagccataaa cttcagttct atcaacaact tcattgaaaa atataagttg    180
gagaactcaa tagaagtagt agaactccat atagaaccat cccctgaact tccacctcat    240
taccacacta caaagaattt gccaacaagt ctcaattcta ccctattaaa ggccattcag    300
acgtcgaatt cgagcttctc agacatcatc agaacattga aacctgaact agtgatatat    360
gatgtgtttc aaccttgggc tgccaagatt gcttcctcac aaggtattcc tgctgtttat    420
ttttctagct ttggaggggc accattatca cttatgcatc atcaccacac gtacggaaaa    480
cccgaatttc ccttccaagc aatagttgtt gaggacatcg aactggaaag tttgctctct    540
ttgtttgatt tcttgtatgc caacatattt gaagtggatc aagattatct ttttgggaat    600
ttcaagcaat cttgtgagct tgttttgtta aagagtagta aagggattga gaggaagtac    660
atcgattatc tttcatcttt gtctcagaaa aaaatattac ctgttggacc actagtcaca    720
gttgacaata agaccaatga ggagaattcc gagatcatga attggttgag caagaaaaaa    780
caccattcaa ctgtctacat ttccttcggt agtgaatact tcctgtctaa agaagagatt    840
gaagagatag caaaagggct tgagctttgt gatgttaact ttatatggat catcagattt    900
ccagttggag tgaccgttaa cttagaagaa acactgcctc aaggtttcct tcaaggggtg    960
aacgaacggg ggatggttgt ttcaggatgg gcaccacaga gcaacatatt agcacatcca   1020
agcacaggag gctttgtgag tcactgtggg tggagttcta tcacagaaag cgtatatttt   1080
ggtgttccgg tcatagggat ggcaatgaaa cttgatcagc aataaacgc  cagaatgtta   1140 tcagaggctg gtagttgtgt cgaagtcaaa agatatgaaa atgaagtgtt taggggagaa   1200
gagatagcga aggcgataaa gaaggtgatt gttgaggaca gtggagaaag gctgcggcaa   1260
agagctttag aattgagcga gaagatgaaa atggaagagg aaaatgagat ggatgaagta   1320
actgagcagc tgtgggagct ttgcttgacg aaaaaacggt aa                      1362
```

```
<210> SEQ ID NO 31
<211> LENGTH: 1437
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 31
atggaacctc atatagttat attcccgttc atgtccaaag gccacacaat ccctctcctc     60
cacctctccc acctcctcct tagtcgcgga gtacgcgtaa cgatcttcac cactgcacaa    120
aaccacccct tcatcgctca acatgtccca aaaacaaata atgttaccat cattgaccta    180
ccgttccctg ataacatccc tggaatttca ccaggaacgg agagcacgga caaactcccg    240
tcgatgtctc tcttcgtccc gttcgtgaac gccgctaaat cgatgcaacc gttcttcgaa    300
gatgagcttg agaaaattca ttcaggggtt agttgtgtta tatcggatgg ttttcttcat    360
tggacgctga atcagcatc caagttcgga attccacgac tgagtttcta cggtatgagc    420
tactatgcct tgacaatttt tcgagtcgct atctcaaaca agttaatatc attgcacgag    480
tcaccgcacg aggcattcac cttacctagt tttccttgga ttaaactcac tagagatcac    540
ttcgacaaac cacttgatca acgtgaacca atggtccgc aatttgactt tttcatggaa    600
gcaacgacag ctactgtgaa tagctatggt ttcttagtga atagcttcta tgagcttgaa    660
ccaactttcg cggattacta tgacaacaat tacaaaccca aggcgtggag tgtcgggcct    720
ctctgcctcg cacaaacgcc aaagaatgat aatctctcgt cgaagcctga gtggattcat    780
tggcttgacc aaaagttgga acaagatcgc cctgttttgt acattgcatt cggatcacaa    840
gcagaaatta cactagaaca gttacatgaa atctcacgag ggttggaaga gtcaaatgta    900 cacttttttgt gggttttaag gaacaatgga gttgaactaa gtgatggatt tgaagacagg    960
gttaagaata gaggaattgt agtaaaagaa tgggttgatc aaagagagat tcttgaacat   1020
gaaagtgtaa aaggctttct aagtcattgc ggctggaatt cggtaatgga aggtatatgt   1080
gcggaggttc tgattcttgc gtggccaatg atagcggagc aacacttgaa tgcaaagatg   1140
gtgagtgaag aaataaagat tggtttgaga gttgaaacgg ttgatggaac ggcaaaggga   1200
tttgtgactg cggcgagttt gacgaaggcg gtgatggaat tgatggaggg tgagaagggg   1260
aaggaattga gggagaatgt gaagaaagtg gcggggggcag cgagggaagc ggtggtggaa   1320
ggtggttcgt cgtggaatgg tttgaatgaa ctcattgatg aggtgtgtag gcataaggaa   1380
atgagtggta gttctaaagt tgatgaaaac aagagggaaa ttaaggatat taattaa     1437

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cccatgggag aagaatacaa gaaa                                              24

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 33
ggtacctata aaatttggta gttaaa                                          26

<210> SEQ ID NO 34
<211> LENGTH: 1080
<212> TYPE: DNA
<213> ORGANISM: Homo sapiens

<400> SEQUENCE: 34
caccgattac atgacgtaca tgttcaagta cgacagtgtt catggtcagt ggaaacacca     60
cgagttgaag gtacaggatg agaagaccct tctgtttggt gaaaagccag taagagtctt    120
gtcaactggt gtcttcacgg acaaagataa ggctgctgct cacttgaagg gtggtgccaa    180
gaaggttgtg atctcagcac caagcaaaga tgcaccaatg tttgttgtgg gtgtcaatga    240
gaaggaatac aaaccagagt tggacattgt ttccaatgct agttgcacta ccaattgcct    300
tgcccctttg gccaaggtca ttaatgatag atttggaatt gttgagggcc tcatgaccac    360
cgtccactct attaccgcaa ctcaaaagac tgtcgatggg ccatcgagca aggactggag    420
aggtggaaga gctgcatcgt tcaacattat ccccagcagc actggtgcag ctaaggctgt    480
tggtaaagtg ctcccagttc tcaatggaaa gctaacggga atggccttcc gtgttcctac    540
tgtcgatgtc tccgtagtgg acctcactgt caggctcgag aaagaggcca cttatgatga    600
gatcaaagct gctatcaagg aggaatccga gggcaacctt aagggcattt tgggctatac    660
cgaagatgat gtggtgtcaa cagactttgt tggtgatagc cgatcaagca ttttcgatgc    720
caaggctgga attgcattga gcaagacgtt tgtgaagctt gtgtcgtggt acgacaacga    780
atggggttac agttcccgtg tgatcgacct gatcgtgcac atggcctcag tttctaaggc    840
ttgatcgatg atctgcttag gccgtgaagc agcttttgtc ttatcgcatc ttttctgagt    900
ttgtaataat gggcttttgt gttatttgca gcctaatttt gcagtttgca aatttatggt    960
ttttggttat gttttgctga aacctatttt attacccttt cgcgttgggt tattgaatgt   1020
gaactctttt tactgatgtg tttaacgttc tctcttttaa aaaaaaaaaa aaaaaaaaa   1080

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgttgctgtt aacgatccat                                                 20

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
agctcttcca cctctcca                                                   18

<210> SEQ ID NO 37
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 37
atgttcaaaa atcctaatat ccgc                                            24

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttagccatca agctcaatct tgaca                                           25

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aacagctatg accatg                                                     16

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctttaccat ggagtaatga gctt                                            24

<210> SEQ ID NO 41
<211> LENGTH: 1367
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 41
gtatgtatgt atgtatgcta tatacgagtc gataaagttg atcgttttca ttttcgacaa     60
atacaaacct cgtgagagaa tcttctcgat catatggcac gagcaggacc actaacccta   120
acttcgctag cgctcgagaa atcgctgcat gaaaagttta tagggacgag acgagagg    180 cctaacttag catacgatca atttagcagt cagattccat tgatctctct ctctgggatc   240
gacgatgaat gtaataagag gaaagagctg tgcaagagaa tagcgcaggc atgcgaagat   300
tggggtattt ttcaagtgat cgatcatggg atcgatttga aactcgtcaa cgatatgact   360
cgtttggctc gtgagttctt cgatttgccc gacgaagaga agctgaggtt cgatatgtct   420
ggtgggagaa aaggaggttt cattgtttcg agccaccttc agggcgaggt ggtccaagac   480
tggcgcgaga tcgtgaccta cttcacatac cctatcaaag gccgtgacta ttccctgtgg   540
cccgacaagc ccgaggcatg gcgggccgtg acagagacct acagctcgca gctaatgtgc   600
ctgggctgca aattgctagg aatcctatcc gaggcaatgg gcctcgaaag agaagcgctg   660
```

```
accaaggcct gtctgaacat ggaccaaaaa gttgtggtca acttttaccc aaaatgccct    720
cagcccaatt tgacattggg cctgaagagg cactcggacc caggtttgat cactctgctg    780
tttcaggata acgttggcgg gcttcaagcg actcgagacg gcgggaagtc gtggatcacg    840
gtccagcccg ttgagggtgc attcgtggtc aatcttggtg attttgctca ttacttgagc    900
aatggaaggt tcaagaacgc ggatcatcga gcggtggtga attcaaacac gaatagaatg    960
tcgatcgcga cgtttcaaaa cccatcgcca gaggctatcg tgtaccctct caagatcgga   1020
gacgacggga agcccattat agaaaagccc atcacttatg agaaatgta caagaggaag   1080 atggctaaag acattgaact tgccaagctc aagaagctag ccaaggaaca aaagttgcaa   1140
gaagaagttg ttaataatgt tgaagatcat catcttaaca atgggaaaac taaataggag   1200
gttaaggtct ttaaggaaac tgacgttgtc ttgtgattgt tatatattct ctatgtcgta   1260
ttcgtcttaa ggttgtcaga tgaaaatatc gaccatgtta ggtatttaat ttatatgaat   1320
tgtattgcct agtcggccat attatgatta aaaaaaaaaa aaaaaaa               1367

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttctctgtcg acgcccattg cc                                              22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgccgtgtcg actcgcttga ag                                              22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aattatttcc caatgttcaa aaat                                            24

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tggagcttta ggtttgtgaa a                                               21

<210> SEQ ID NO 46
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 46
atgggagaag aatacaagaa aac                                           23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcttacgata aacaaactc a                                              21

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atcatcgagc ggtggtgaa                                                19

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tggccgacta ggcaatacaa t                                             21

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cccttctgtt tggtgaaaag cc                                            22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cctcggattc ctccttgata gc                                            22

<210> SEQ ID NO 52
<211> LENGTH: 29
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 52
cccatatata gccatggaag ataccatcg                                    29

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tagtgttgtg gagtcggggg atttcg                                       26

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aatgggatgc ttccgacttc t                                            21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagtggtttc tgccattgct t                                            21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
aggaaaaaac aggctgaaaa                                              20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
catcgagcgg tggtgaatt                                               19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 58
ctggcgatgg gttttgaaa                                                       19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
aaacacgaat agaatgtcg                                                       19

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaagatgacc ttgcggtgat tt                                                   22

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttgtcctctt cccctttata ggttt                                                25

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
agttcgccgg gagtttcgtg agtctg                                               26

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggttggcccg catttca                                                         17

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
```

```
tagaaaaccc tccggcagaa                                                  20

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
agatggactt aaatgcg                                                     17

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcattgagca agacgtttgt g                                                21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acgggaactg taaccccatt c                                                21

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
agcttgtgtc gtggtacg                                                    18

<210> SEQ ID NO 69
<211> LENGTH: 2220
<212> TYPE: DNA
<213> ORGANISM: Linaria bipartita
<220> FEATURE:
<221> NAME/KEY: CDS
<222> LOCATION: (127)..(1488)

<400> SEQUENCE: 69
tggacactga catggactga aggagtagaa ataccaaaag ttttcaaact ctttattgca       60
atatacttgt acaaatctac tgcaactaaa acctattatt aattatatat atacccatat      120 atagat atg gaa gat acc atc gta ttt tac act cca agc gat cac agt        168
       Met Glu Asp Thr Ile Val Phe Tyr Thr Pro Ser Asp His Ser
         1               5                   10 caa ccc aca ata gcg ttg gca aag ttc atc agc aaa cac cac cct tcc        216
Gln Pro Thr Ile Ala Leu Ala Lys Phe Ile Ser Lys His His Pro Ser
 15                  20                  25                  30 atc tcc atg aca atc atc agc acc gcc gca ttc cct tcg tcc gca gcg        264
Ile Ser Met Thr Ile Ile Ser Thr Ala Ala Phe Pro Ser Ser Ala Ala
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
|       |       |       | 35    |       |       |       | 40    |       |       |       | 45    |       |       |       |       |      |
| gtg   | ctg   | cct   | aaa   | aca   | ata   | agt   | tac   | cac   | ccc   | ctc   | ccc   | gcc   | gtg   | ccc   | atg   | 312  |
| Val   | Leu   | Pro   | Lys   | Thr   | Ile   | Ser   | Tyr   | His   | Pro   | Leu   | Pro   | Ala   | Val   | Pro   | Met   |      |
|       |       |       | 50    |       |       |       | 55    |       |       |       | 60    |       |       |       |       |      |
| ccc   | ccg   | aac   | ctc   | tcc   | tcc   | aat   | ccc   | gtg   | gaa   | ttc   | ctc   | ttc   | gaa   | atc   | ccc   | 360  |
| Pro   | Pro   | Asn   | Leu   | Ser   | Ser   | Asn   | Pro   | Val   | Glu   | Phe   | Leu   | Phe   | Glu   | Ile   | Pro   |      |
|       |       |       | 65    |       |       |       | 70    |       |       |       | 75    |       |       |       |       |      |
| cga   | ctc   | cac   | aac   | act   | aaa   | ctc   | cgc   | gaa   | gca   | ctc   | gaa   | aga   | atc   | tcc   | gag   | 408  |
| Arg   | Leu   | His   | Asn   | Thr   | Lys   | Leu   | Arg   | Glu   | Ala   | Leu   | Glu   | Arg   | Ile   | Ser   | Glu   |      |
|       |       | 80    |       |       |       |       | 85    |       |       |       |       | 90    |       |       |       |      |
| aca   | tca   | aag   | atc   | aag   | gcg   | ttg   | gtt   | atc   | gat   | ttc   | ttt   | tgc   | aac   | tcc   | gct   | 456  |
| Thr   | Ser   | Lys   | Ile   | Lys   | Ala   | Leu   | Val   | Ile   | Asp   | Phe   | Phe   | Cys   | Asn   | Ser   | Ala   |      |
|       | 95    |       |       |       | 100   |       |       |       | 105   |       |       |       | 110   |       |       |      |
| ttc   | gaa   | gtt   | tcc   | agg   | agc   | ttg   | aac   | att   | ccg   | aca   | ttc   | ttc   | gaa   | gcc   | agc   | 504  |
| Phe   | Glu   | Val   | Ser   | Arg   | Ser   | Leu   | Asn   | Ile   | Pro   | Thr   | Phe   | Phe   | Glu   | Ala   | Ser   |      |
|       |       |       |       | 115   |       |       |       | 120   |       |       |       | 125   |       |       |       |      |
| ctc   | ggc   | gcg   | tcc   | ggg   | ctc   | tgc   | gag   | ttt   | ctc   | tac   | cac   | ccg   | aca   | ttt   | cac   | 552  |
| Leu   | Gly   | Ala   | Ser   | Gly   | Leu   | Cys   | Glu   | Phe   | Leu   | Tyr   | His   | Pro   | Thr   | Phe   | His   |      |
|       |       |       | 130   |       |       |       | 135   |       |       |       | 140   |       |       |       |       |      |
| aaa   | acc   | gtc   | ccc   | gga   | gac   | atc   | gcg   | gac   | ttc   | aac   | gac   | ttt   | ctt   | gaa   | atc   | 600  |
| Lys   | Thr   | Val   | Pro   | Gly   | Asp   | Ile   | Ala   | Asp   | Phe   | Asn   | Asp   | Phe   | Leu   | Glu   | Ile   |      |
|       |       |       | 145   |       |       |       | 150   |       |       |       | 155   |       |       |       |       |      |
| ccg   | ggg   | tgc   | cct   | ccg   | ctt   | cac   | tcg   | gct   | gat   | gtc   | cct   | aag   | ggt   | ttg   | ttc   | 648  |
| Pro   | Gly   | Cys   | Pro   | Pro   | Leu   | His   | Ser   | Ala   | Asp   | Val   | Pro   | Lys   | Gly   | Leu   | Phe   |      |
|       |       | 160   |       |       |       |       | 165   |       |       |       |       | 170   |       |       |       |      |
| cga   | cgc   | aag   | act   | att   | gct   | tac   | aaa   | cac   | ttc   | ctc   | gac   | act   | gcc   | aac   | aac   | 696  |
| Arg   | Arg   | Lys   | Thr   | Ile   | Ala   | Tyr   | Lys   | His   | Phe   | Leu   | Asp   | Thr   | Ala   | Asn   | Asn   |      |
| 175   |       |       |       |       | 180   |       |       |       |       | 185   |       |       |       |       | 190   |      |
| atg   | cgg   | atg   | tcg   | agt   | gga   | atc   | ctc   | tta   | cac   | gcg   | ttc   | gat   | gcg   | ctt   | gaa   | 744  |
| Met   | Arg   | Met   | Ser   | Ser   | Gly   | Ile   | Leu   | Leu   | His   | Ala   | Phe   | Asp   | Ala   | Leu   | Glu   |      |
|       |       |       | 195   |       |       |       | 200   |       |       |       | 205   |       |       |       |       |      |
| tac   | cga   | gct   | aag   | gaa   | gct   | ttg   | tcc   | aac   | ggc   | ttg   | tgc   | aat   | ccg   | gac   | ggg   | 792  |
| Tyr   | Arg   | Ala   | Lys   | Glu   | Ala   | Leu   | Ser   | Asn   | Gly   | Leu   | Cys   | Asn   | Pro   | Asp   | Gly   |      |
|       |       |       | 210   |       |       |       | 215   |       |       |       | 220   |       |       |       |       |      |
| cca   | act   | ccg   | cct   | gtt   | tac   | ttt   | gtt   | tcg   | cct   | act   | gtg   | gct   | gaa   | aca   | ttg   | 840  |
| Pro   | Thr   | Pro   | Pro   | Val   | Tyr   | Phe   | Val   | Ser   | Pro   | Thr   | Val   | Ala   | Glu   | Thr   | Leu   |      |
|       |       |       | 225   |       |       |       | 230   |       |       |       | 235   |       |       |       |       |      |
| gca   | tac   | agg   | gaa   | aac   | acc   | gcc   | gcc   | ttg   | cgg   | cat   | gaa   | tgc   | ttg   | acg   | tgg   | 888  |
| Ala   | Tyr   | Arg   | Glu   | Asn   | Thr   | Ala   | Ala   | Leu   | Arg   | His   | Glu   | Cys   | Leu   | Thr   | Trp   |      |
|       |       |       | 240   |       |       |       | 245   |       |       |       | 250   |       |       |       |       |      |
| ctt   | gat   | ttg   | cag   | cct   | gat   | aaa   | agc   | gtt   | atc   | ttc   | ctt   | tgt   | ttt   | gga   | agg   | 936  |
| Leu   | Asp   | Leu   | Gln   | Pro   | Asp   | Lys   | Ser   | Val   | Ile   | Phe   | Leu   | Cys   | Phe   | Gly   | Arg   |      |
| 255   |       |       |       |       | 260   |       |       |       |       | 265   |       |       |       |       | 270   |      |
| agg   | gga   | aca   | ttc   | tcc   | atg   | caa   | cag   | ttg   | cat   | gaa   | att   | gct   | gtc   | ggt   | ctt   | 984  |
| Arg   | Gly   | Thr   | Phe   | Ser   | Met   | Gln   | Gln   | Leu   | His   | Glu   | Ile   | Ala   | Val   | Gly   | Leu   |      |
|       |       |       | 275   |       |       |       | 280   |       |       |       | 285   |       |       |       |       |      |
| gaa   | cgg   | agc   | ggg   | cga   | aga   | ttt   | ctc   | tgg   | gcc   | atc   | cgc   | agt   | agt   | ggg   | gca   | 1032 |
| Glu   | Arg   | Ser   | Gly   | Arg   | Arg   | Phe   | Leu   | Trp   | Ala   | Ile   | Arg   | Ser   | Ser   | Gly   | Ala   |      |
|       |       |       | 290   |       |       |       | 295   |       |       |       | 300   |       |       |       |       |      |
| ggg   | aac   | ggt   | gag   | cct   | gac   | ttg   | agc   | gtg   | gtg   | ctg   | ccg   | gag   | ggt   | ttc   | ttg   | 1080 |
| Gly   | Asn   | Gly   | Glu   | Pro   | Asp   | Leu   | Ser   | Val   | Val   | Leu   | Pro   | Glu   | Gly   | Phe   | Leu   |      |
|       |       | 305   |       |       |       |       | 310   |       |       |       |       | 315   |       |       |       |      |
| gag   | aga   | acc   | aaa   | gat   | att   | ggg   | ctg   | gtg   | ata   | acg   | aca   | tgg   | gcg   | ccg   | cag   | 1128 |
| Glu   | Arg   | Thr   | Lys   | Asp   | Ile   | Gly   | Leu   | Val   | Ile   | Thr   | Thr   | Trp   | Ala   | Pro   | Gln   |      |
|       |       | 320   |       |       |       |       | 325   |       |       |       |       | 330   |       |       |       |      |
| aaa   | gag   | gtg   | tta   | agc   | cat   | gtg   | gcc   | gtg   | tgt   | gga   | ttt   | gtg   | acg   | cac   | tgc   | 1176 |
| Lys   | Glu   | Val   | Leu   | Ser   | His   | Val   | Ala   | Val   | Cys   | Gly   | Phe   | Val   | Thr   | His   | Cys   |      |
| 335   |       |       |       |       | 340   |       |       |       |       | 345   |       |       |       |       | 350   |      |
| ggc   | tgg   | aac   | tca   | gtt   | ctc   | gag   | gcg   | gtg   | tcg   | ttt   | ggg   | gtt   | ccg   | atg   | att   | 1224 |
| Gly   | Trp   | Asn   | Ser   | Val   | Leu   | Glu   | Ala   | Val   | Ser   | Phe   | Gly   | Val   | Pro   | Met   | Ile   |      |

```
                355                 360                 365
ggg tgg ccg ctg tac gca gag cag agg atg aat cgg gtg ttt atg gtg    1272
Gly Trp Pro Leu Tyr Ala Glu Gln Arg Met Asn Arg Val Phe Met Val
            370                 375                 380 gag gaa ata aag gtg gca ttg cct ttg gag gag gag gcg gat ggg ttg    1320
Glu Glu Ile Lys Val Ala Leu Pro Leu Glu Glu Glu Ala Asp Gly Leu
        385                 390                 395 gtg agg gcg aca gaa ttg gag aag cgg gtg aga gag ttg acc gag tcc    1368
Val Arg Ala Thr Glu Leu Glu Lys Arg Val Arg Glu Leu Thr Glu Ser
    400                 405                 410 gtg agg gga aaa gcg gta agc cgg cgg gtg gag gaa atg aga ctc tcg    1416
Val Arg Gly Lys Ala Val Ser Arg Arg Val Glu Glu Met Arg Leu Ser
415                 420                 425                 430 gca gag aag gcc gtg agc aag ggt gga acg tcg ctg att gca ttg gag    1464
Ala Glu Lys Ala Val Ser Lys Gly Gly Thr Ser Leu Ile Ala Leu Glu
                435                 440                 445 aaa ttc atg gac tcg att act cta taagcgtaag agttgctata aatttagcta   1518
Lys Phe Met Asp Ser Ile Thr Leu
                450 tgttgcacgg atacgtcaaa taaaccttgc tcgtattctt agatacgtat actatacaaa   1578
tacaatttat gaataagttt ttcatatggc gtatgaagta ttctaattaa attaaataac   1638
acgttttgaa gcgttattat aagggcgtaa ctagtaaata ataagaaata attaaacaaa   1698
aaaaaattat gatgttaatg ataatttttat taatatttta tactataaag ttcttaatat   1758
tcttgttgat atgtaagttt attatataag tatttttaagt gttttatttg gtattttgaa   1818
tttaagtacc atcgtggaat acttttatat gagcttataa ttttaatgtt gaatagattt   1878
catattaata tgttattatt tatgtgaaca aaaatatta ttgctcaagt tattttgaat    1938
tatattttta tatatataag tatttgatat aaaatattta acgtattatg tgcgtatcct   1998
tatttttacaa agttacccgt attcgtttca tgtttgatac attttttcat attcgtatat   2058
gtgcccgtgt ccgtgcaata tagtaaatta gttatggtat gtgatgtttc tatgttgtaa   2118
caaaataatg gtacttaatt tgaatagtcc agtcaagtat ttgtaatgtt aaattaatat   2178
tccatttaat attccattat tctctcaaaa aaaaaaaaaa aa                     2220

<210> SEQ ID NO 70
<211> LENGTH: 454
<212> TYPE: PRT
<213> ORGANISM: Linaria bipartita

<400> SEQUENCE: 70

Met Glu Asp Thr Ile Val Phe Tyr Thr Pro Ser Asp His Ser Gln Pro
1               5                   10                  15

Thr Ile Ala Leu Ala Lys Phe Ile Ser Lys His Pro Ser Ile Ser
            20                  25                  30

Met Thr Ile Ile Ser Thr Ala Ala Phe Pro Ser Ala Ala Val Leu
        35                  40                  45

Pro Lys Thr Ile Ser Tyr His Pro Leu Pro Ala Val Pro Met Pro Pro
    50                  55                  60

Asn Leu Ser Ser Asn Pro Val Glu Phe Leu Phe Glu Ile Pro Arg Leu
65                  70                  75                  80

His Asn Thr Lys Leu Arg Glu Ala Leu Glu Arg Ile Ser Glu Thr Ser
                85                  90                  95

Lys Ile Lys Ala Leu Val Ile Asp Phe Phe Cys Asn Ser Ala Phe Glu
            100                 105                 110

Val Ser Arg Ser Leu Asn Ile Pro Thr Phe Phe Glu Ala Ser Leu Gly
```

```
                115              120                125
Ala Ser Gly Leu Cys Glu Phe Leu Tyr His Pro Thr Phe His Lys Thr
        130             135             140

Val Pro Gly Asp Ile Ala Asp Phe Asn Asp Phe Leu Glu Ile Pro Gly
145                 150              155                 160

Cys Pro Pro Leu His Ser Ala Asp Val Pro Lys Gly Leu Phe Arg Arg
            165             170             175

Lys Thr Ile Ala Tyr Lys His Phe Leu Asp Thr Ala Asn Asn Met Arg
            180             185             190

Met Ser Ser Gly Ile Leu Leu His Ala Phe Asp Ala Leu Glu Tyr Arg
        195             200             205

Ala Lys Glu Ala Leu Ser Asn Gly Leu Cys Asn Pro Asp Gly Pro Thr
        210             215             220

Pro Pro Val Tyr Phe Val Ser Pro Thr Val Ala Glu Thr Leu Ala Tyr
225             230             235                 240

Arg Glu Asn Thr Ala Ala Leu Arg His Glu Cys Leu Thr Trp Leu Asp
                245             250             255

Leu Gln Pro Asp Lys Ser Val Ile Phe Leu Cys Phe Gly Arg Arg Gly
            260             265             270

Thr Phe Ser Met Gln Gln Leu His Glu Ile Ala Val Gly Leu Glu Arg
        275             280             285

Ser Gly Arg Arg Phe Leu Trp Ala Ile Arg Ser Ser Gly Ala Gly Asn
    290             295             300

Gly Glu Pro Asp Leu Ser Val Val Leu Pro Glu Gly Phe Leu Glu Arg
305             310             315             320

Thr Lys Asp Ile Gly Leu Val Ile Thr Thr Trp Ala Pro Gln Lys Glu
            325             330             335

Val Leu Ser His Val Ala Val Cys Gly Phe Val Thr His Cys Gly Trp
            340             345             350

Asn Ser Val Leu Glu Ala Val Ser Phe Gly Val Pro Met Ile Gly Trp
        355             360             365

Pro Leu Tyr Ala Glu Gln Arg Met Asn Arg Val Phe Met Val Glu Glu
    370             375             380

Ile Lys Val Ala Leu Pro Leu Glu Glu Glu Ala Asp Gly Leu Val Arg
385             390             395             400

Ala Thr Glu Leu Glu Lys Arg Val Arg Glu Leu Thr Glu Ser Val Arg
            405             410             415

Gly Lys Ala Val Ser Arg Arg Val Glu Glu Met Arg Leu Ser Ala Glu
            420             425             430

Lys Ala Val Ser Lys Gly Gly Thr Ser Leu Ile Ala Leu Glu Lys Phe
            435             440             445

Met Asp Ser Ile Thr Leu
450
```

METHOD FOR PRODUCING YELLOW FLOWER BY CONTROLLING FLAVONOID SYNTHETIC PATHWAY

CROSS REFERENCE TO RELATED APPLICATIONS

This application is a division of application Ser. No. 10/583,110, filed Jun. 15, 2006, now U.S. Pat. No. 7,750,209, which is a National Stage of International Application No. PCT/JP2004/019461, filed Dec. 17, 2004, which claims the benefit of Japanese Patent Application No. 2003-420046, filed on Dec. 17, 2003, and which are incorporated by reference herein in their entirety.

Reference to a Sequence Listing

A Sequence Listing containing SEQ ID NOS: 1-70 is incorporated herein by reference.

TECHNICAL FIELD

The present invention relates to a gene coding for a protein having activity of transferring sugars to chalcones, and to plants with modified flower color utilizing the gene. More specifically, the invention relates to a gene coding for a protein having activity of synthesizing chalcone 4'-glucoside, and preferably to a gene derived from the family Scrophulariaceae, and more preferably *Antirrhinum majus* or *Linaria bipartita*, coding for a protein having activity of synthesizing chalcone 4'-glucosides, as well as to a method for modifying flower color, and preferably a method for modifying flower color to yellow, by expressing these genes and an aureusidin synthase (hereinafter, "AS") gene either separately or simultaneously and accumulating chalcones or aurones.

BACKGROUND ART

Flower color is an important feature for the appreciation and purchasing of ornamental flowers, and flowers with a large variety of colors have traditionally been bred. It is rare for a single species to possess flowers of all colors, as the biosynthesis of pigments that appear as flower colors is genetically determined. Because the gene sources that can be used in hybridization breeding are limited to crossable related varieties, it is essentially impossible to produce flowers of all colors in a target variety by hybridization breeding. Recently, gene recombination techniques have made it possible to obtain flower pigment-synthesizing genes from certain plants and express those genes in different species in order to achieve modified flower color (Plant Cell Physiol. 39, 1119 (1998), Curr. Opin. Biotechnol. 12, 155 (2001)).

The flower colors of orange, red, violet and blue are exhibited primarily by flavonoids known as anthocyanins. Yellow colors generally derive from non-flavonoid compounds such as carotenoids and betalains, but the yellow colors of some plant species are due to flavonoids. For example, yellow carnations are known to possess 4,2',4',6'-tetrahydroxychalone (hereinafter, THC) 2-glucoside in their flower petals (Phytochemistry 5, 111 (1966)). THC 4'-glucoside is also found in *Antirrhinum majus* and *Linaria bipartita*.

Chalcones such as, THC, butein, isoliquiritigenin and their glycosilated derivatives are known; for example, the aglycon of the glucosides in carnations, morning glory, peony, aster, strawflower, periwinkle, cyclamen and petunia is THC, in *Antirrhinum majus* (snapdragon) and statice it is 3,4,2',4',6'-pentahydroxychalcone (PHC), in cosmos and Jerusalem artichoke it is butein, and in dahlia it is butein and isoliquiritigenin. Also, certain limited species such as snapdragon, *Linaria bipartita* (toadflax) and morning glory contain yellow flower pigments known as aurones, including aureusidin (hereinafter, AU) and bracteatin.

Because the absorption maxima for aurones are between 399 and 403 nm, compared to absorption maxima between 372 and 382 nm for chalcones, their color tones differ and the fluorescence emitted gives aurones a sharper yellow color (Biohorti 1, 49-57 (1990), Seibundo Shinkosha). Chalcones, aurones and anthocyanins usually accumulate as glucosides in the vacuoles of plant cells. The biosynthetic pathway of anthocyanins has been thoroughly studied, and the enzymes involved in anthocyanin synthesis and their coding genes are known (Comprehensive Natural Products Chemistry, vol I (ed. Sankawa) pp 713-748, Elsevier, Amsterdam (1999)).

The biosynthetic pathway of flavonoids is widely distributed among the higher plants and is conserved among species. THC is biosynthesized from three molecules of malonyl CoA and one molecule of coumaroyl CoA, by the catalytic action of chalcone synthase. THC exhibits a light yellow color, but in plant cells it is usually rapidly converted to colorless naringenin by chalcone isomerase (CHI). Also, THC is highly unstable at near neutral pH and is converted to naringenin by spontaneous ring closure. For THC to exist stably in plant cells, i.e. for it to stably exhibit a yellow color, the 2'-position of THC must be modified with a saccharide to prevent its ring closure. The reaction is catalyzed by an enzyme that transfers glucose to the 2'-position of THC (UDP-glucose: 4,2',4',6'-tetrahydroxychalcone 2'-glucosyltransferase, hereinafter abbreviated as 2'CGT).

THC 2'-glucoside is present in carnation and cyclamen, and therefore 2'CGT is also predicted to be found in their flowers. Thus, it was conjectured that if the 2'CGT gene could be obtained and the enzyme gene expressed in a plant, it should be possible to accumulate THC 2'-glucosides and produce yellow flowers (Biotechnology of Ornamental Plants, Edited by Geneve, Preece and Merkle, pp 259-294, CAB International Wallingford, UK (1997)). Moreover, it was discovered that adequately accumulating THC 2'-glucoside and exhibiting yellow color requires deletion of the CHI gene to suppress enzymatic conversion from THC to naringenin, and that a clear yellow color also requires deletion of the gene for flavanone 3-hydroxylase (hereinafter abbreviated as F3H) in addition to the CHI gene (*Plant Cell Physiol.* 43, 578 (2002)).

While cloning of the carnation 2'CGT gene has been reported to date (*Plant Cell Physiol.* 44, s158 (2003)), its sequence has not been published. Also, the gene coding for 2'CGT activity has been obtained from carnation and expressed in petunia, thereby accumulating THC 2'-glucoside in petunia petals (PCT/JP03/10500). However, the THC 2'-glucoside produced by 2'CGT does not have a chemical structure that can serve as a precursor for aurone synthesis. Also, as mentioned above, accumulation of THC 2'-glucoside results in only light yellow petals.

It is known that faint yellow petals are produced by accumulation of THC having the 2'-hydroxyl methylated, but the nature of the enzyme that catalyzes this methylation and of its gene is unknown. Yellow varieties such as dahlia and cosmos contain 6'-deoxychalcone. In legumes, 6'-deoxychalcone is the precursor of 5-deoxyflavonoid, which is synthesized by the catalytic action of chalcone synthase (CHS) and chalcone reductase (CHR). It has been reported that introduction of the alfalfa CHR gene into petunia produced 6'-deoxychalcones such as butein, and that when the CHR gene was introduced into white flower petunia the flowers were mostly white upon blooming although a very light yellow color was observed at the budding stage, and therefore it was not possible to create an industrially useful yellow flower (Plant J. 13, 259 (1998)).

Because aurones exhibit a more brilliant yellow color than chalcone glucosides as explained above, it would be highly useful, for the industry, to develop a method for accumulating aurones. AS, one of the enzymes involved in aurone biosynthesis, and its gene, have already been reported in the literature (Science, 290, 1163 (2000)). According to this report, AS produces AU, bracteatin and their glucosides from THC, PHC and their glucosides as substrates. However, use of the AS gene to produce and accumulate aurones such as AU and bracteatin has not been described.

The present inventors have constructed a binary vector having the AS gene linked downstream from a structural promoter and introduced the AS gene into petunia and torenia by the *Agrobacterium* method, but no accumulation of aurones was observed. It has also been reported that 3-glucosylation of anthocyanidin is essential for transportation of anthocyanins into vacuoles (Nature 375, 397 (1995)), suggesting that glucosylation of aurones is likewise necessary as a transportation signal into vacuoles. In fact, the major aurone that accumulates in yellow *Antirrhinum majus* flower petals is AU 6'-glucoside. A GT exhibiting AU 6'-glucosylating activity (AU6GT) (WO 00/49155) was therefore obtained, and the AU6GT gene was constitutively expressed in petunia together with the AS gene, but accumulation of aurones was not observed.

The enzymes involved in flavonoid and anthocyanin biosynthesis are believed to localize in the cytoplasm or endoplasmic reticulum of cells. By the actions of these enzymes, flavonoids and anthocyanins are synthesized and glucosylated outside of vacuoles, i.e. in the cytoplasm, and transported into the vacuoles (Natural Product Reports 20, 288, (2003)). However, ardent research led the present inventors to the finding that AS is exceptional in that it localizes in the vacuoles. Thus, it was hypothesized that glucosylated chalcones may be transported to the vacuoles in vivo and used as substrates for synthesis of aurones in the vacuoles.

As mentioned above, AU 6'-glucoside is the major aurone that accumulates in the vacuoles of yellow *Antirrhinum majus* petals. The 6' position of AU corresponds to the 4' position of THC, and THC 4'-glucosides are also present in yellow *Antirrhinum majus* petals. On this basis, an aurone synthetic pathway was inferred wherein glucosylation of the 4' position of THC synthesized in the cytoplasm is followed by transport to the vacuoles, and this is used as substrate for synthesis of AU 6'-glucosides by AS. Thus, it was concluded that synthesis of THC 4'-glucoside is essential for synthesis of aurones such as AU 6'-glucoside in different plant varieties. For this purpose, UDP-glucose: 4,2',4',6'-tetrahydroxychalcone 4'-glucosyltransferase (hereinafter, 4'CGT) is required for 4'-glucosylation of THC, and therefore the 4'CGT gene must be obtained. However, cloning of the 4'CGT gene has not yet been reported, nor do reports exist of isolating 4'CGT.

Enzymes that catalyze glucosylation of a variety of compounds including flavonoids to produce glucosides are generally referred to as glucosyltransferases (GT), and plants possess a large diversity of GT molecules and their coding genes, corresponding to the types of substrates and transferred sugars. Because GT enzymes usually utilize UDP-glucose as the glucose donor, they contain in their amino acid sequence a motif that binds UDP-glucose (Plant J. 19, 509 (1999)). Already, GT genes carrying this motif are known in 99 species of *Arabidopsis* whose entire genome structure has been elucidated (J, Biol. Chem, 276, 4338, (2001)).

GT enzymes and amino acid sequences and functions have also been worked out in several other plants. The genes for enzymes catalyzing reactions of transferring sugars to the 3-hydroxyl groups of flavonoids or anthocyanidins (UDP-glucose:flavonoid 3-glucosyltransferase, hereinafter: 3GT) have been obtained from perilla, corn, gentian, grape and the like (J. Biol. Chem. 274, 7405 (1999); J. Biol. Chem. 276, 4338, (2001)). In addition, genes for enzymes catalyzing reactions of transferring sugars to the 5-hydroxyl groups of anthocyanins (UDP-glucose:anthocyanin 5-glucosyltransferase, hereinafter: 5GT) have been obtained from perilla, verbena and the like (J. Biol. Chem., 274, 7405, (1999)).

Analysis of the amino acid sequences of 3GT and 5GT has shown that GT enzymes with the same function have similar amino acid sequences even in different plant varieties, or in other words, that they constitute a family (J. Biol. Chem. 276, 4338, (2001)). Thus, it is not difficult to obtain enzymes having the same function as known GT enzymes (i.e., orthologs) from other plant varieties, given the current level of technology. For example, the petunia 5GT gene has been cloned using the perilla 5GT gene (Plant Mol Biol. 48, 401 (2002)). However, much laborious trial and error is required to obtain a novel GT gene having absolutely no known ortholog.

As regards *Arabidopsis* whose entire genome structure is known as mentioned above, its flower petals are white and accumulation of chalcone 4'-glucosides has not been reported. Consequently, *Arabidopsis* GT gene information cannot be used for cloning of the 4'CGT gene. Moreover, even though 2'CGT has been isolated from carnation (PCT/JP03/10500), high homology does not necessarily exist between the 4'CGT gene and the 2'CGT gene. This is because the biochemical and molecular biological features of each GT may differ substantially if the position of sugar addition is different, even if the substrate is the same. This is also supported by the fact that 3GT and 5GT belong to different GT families. Also, betanidine 5GT and 6GT have the same substrates, and yet their amino acid homology has been reported to be only 19% (Planta 214, 492 (2002)).

In fact, the GT enzymes that transfer sugars to the 3-, 5- and 3'-positions of the same anthocyanidin skeleton belong to different families in the GT superfamily, and the amino acid homology between these families is no more than about 20% (Plant Physiol. 132, 1652, (2003), Natural Product Reports 20, 288, (2003)). Several methods are possible for obtaining not only the 4'CGT gene but also novel genes. For example, the genes for enzymes expressed in flower petals, which are involved in the synthesis of rose scent components, have been extensively sequenced and have been identified by their structures, expression patterns and expression in *E. coli* (Plant Cell. 14, 2325 (2002)). In order to identify the 4'CGT gene, 5,000 clones were randomly selected from a cDNA library derived from the petals of yellow *Antirrhinum majus* (Butterfly Yellow variety) which accumulates aurone and chalcone 4'-glucosides, and their nucleotide sequences were determined.

As a result of homology search using a public DNA database, three different GT genes were obtained. Two of the genes were the 3GT gene and the aforementioned AU6GT-coding gene (WO 00/49155), while the remaining gene was for a novel GT (designated as pSPB662) (SEQ ID NO: 13). However, the GT encoded by pSPB662 exhibited no glucosylating activity for THC, and was clearly not 4'CGT. Furthermore, as mentioned above, high expression of this gene together with the AS gene in petunia resulted in no observable production of chalcone glucosides or aurones, nor was any change in flower color seen. These results suggest that a chalcone glucosylating enzyme gene cannot be isolated by random screening of approximately 5,000 clones, and it was therefore difficult to obtain a 4'CGT gene.

Patent document 1: PCT/JP03/10500
Patent document 2: WO 00/49155
Non-patent document 1: Plant Cell Physiol. 39, 1119 (1998)
Non-patent document 2: Curr. Opin. Biotechnol. 12, 155 (2001)
Non-patent document 3: Phytochemistry 5,111 (1966)
Non-patent document 4: Biohorti 1 49-57 (1990) SEIBUNDO SHINKOSHA
Non-patent document 5: Comprehensive Natural Products Chemistry, vol I (ed. Sankawa) pp 713-748, Elsevier, Amsterdam (1999)
Non-patent document 6: Biotechnology of Ornamental Plants, Edited by Geneve, Preece and Merkle, pp 259-294, CAB International Wallingford, UK (1997)
Non-patent document 7: Plant Cell Physiol. 43, 578 (2002)
Non-patent document 8: Plant Cell Physiol. 44, s158 (2003)
Non-patent document 9: Plant J. 13, 259 (1998)
Non-patent document 10: Science, 290, 1163 (2000)
Non-patent document 11: Nature 375, 397 (1995)
Non-patent document 12: Natural Product Reports 20, 288, (2003)
Non-patent document 13: Plant J. 19, 509 (1999)
Non-patent document 14: J. Biol. Chem. 276, 4338, (2001)
Non-patent document 15: J. Biol. Chem. 274, 7405 (1999)
Non-patent document 16: Plant Mol Biol. 48, 401 (2002)
Non-patent document 17: Planta 214, 492 (2002)
Non-patent document 18: Plant Physiol. 132, 1652, 2003 (2003)
Non-patent document 19: Plant Cell. 14, 2325 (2002)

DISCLOSURE OF THE INVENTION

The present invention provides a protein having activity of transferring sugars to the 4'-hydroxyl groups of chalcones, and its gene, and preferably a protein having activity of transferring a sugar to the 4'-hydroxyl groups of chalcones specifically, and its gene. The invention further provides plants with modified flower color, preferably altered to yellow, using the aforementioned GT gene.

As mentioned above, the biochemical and molecular biological features of 4'CGT are unknown, and the enzyme has not been purified nor its gene cloned. The present inventors, using a probe having a nucleotide sequence corresponding to the conserved amino acid sequence of the GT family, obtained ten different GT genes having the nucleotide sequence for the conserved amino acid sequence from a yellow *Antirrhinum majus* (Butterfly Yellow) flower petal cDNA library. The GT gene group was expressed in different *E. coli* cells, activity of transferring glucose to the chalcone 4'-position, i.e. 4'CGT activity, was confirmed among the *E. coli* extracts, and it was confirmed that the cloned gene coded for 4'CGT. The gene was expressed in plants for modification of flower color, and the present invention was thereupon completed.

Specifically, the invention provides (1) a gene coding for a protein having activity of transferring a sugar to the chalcone 4'-position.

The invention further provides (2) a gene according to (1) above coding for the amino acid sequence listed as SEQ ID NO: 2.

The invention further provides (3) a gene according to (1) above, which hybridizes to all or a portion of the nucleotide sequence listed as SEQ ID NO: 1 under conditions of 5×SSC, 50° C. and codes for a protein having activity of transferring a sugar to the chalcone 4'-position.

The invention still further provides (4) a gene according to (1) above, which codes for a protein having the amino acid sequence listed as SEQ ID NO: 2 with a modification of one or a plurality of amino acids that are added, deleted and/or substituted with other amino acids, and having activity of transferring a sugar to the chalcone 4'-position.

The invention still further provides (5) a gene according to (1) above, which hybridizes to DNA comprising all or a portion of the nucleotide sequence listed as SEQ ID NO: 1 under stringent conditions and codes for a protein having activity of transferring a sugar to the chalcone 4'-position.

The invention still further provides (6) a gene according to any one of (1) to (5) above, which is derived from the family Scrophulariaceae.

The invention still further provides (7) a vector comprising a gene according to any one of (1) to (6) above.

The invention still further provides (8) host cells transformed by a vector according to (7) above.

The invention still further provides (9) a protein encoded by a gene according to any one of (1) to (6) above.

The invention still further provides (10) a method of producing a protein having activity of transferring a sugar to the chalcone 4'-position, characterized by culturing or growing host cells according to (7) above and obtaining the protein from the host cells.

The invention still further provides (11) a plant having a gene according to any one of (1) to (6) above introduced therein or a progeny of the plant having the same properties as the plant, or tissue of such a plant.

The invention still further provides (12) a flower cut from a plant according to (11) above.

The invention still further provides (13) a method for transferring a sugar to the chalcone 4'-position using a gene according to any one of (1) to (6) above.

The invention still further provides (14) a plant having modified flower color obtained by introducing and expressing a gene according to any one of (1) to (6) above into the plant, or a progeny of the plant having the same properties as the plant.

The invention still further provides (15) a plant according to (14) above characterized in that the flower color has a yellow tint.

The invention still further provides (16) a method of introducing and expressing a gene according to any one of (1) to (6) above together with a gene coding for aureusidin synthase in a plant to alter the flower color to yellow.

The invention still further provides (17) a method of introducing and expressing a gene according to any one of (1) to (6) above together with a gene coding for aureusidin synthase in a plant, and also inhibiting expression of a flavonoid synthesis pathway gene in the host, to alter the flower color to yellow.

The invention still further provides (18) a method of introducing and expressing a gene according to any one of (1) to (6) above together with a gene coding for aureusidin synthase in a plant, and also inhibiting expression of the dihydroflavonol reductase gene in the host, to alter the flower color to yellow.

The invention still further provides (19) a method of introducing and expressing a gene according to any one of (1) to (6) above together with a gene coding for aureusidin synthase in a plant, and also inhibiting expression of the flavanone 3-hydroxylase gene in the host, to alter the flower color to yellow.

BEST MODE FOR CARRYING OUT THE INVENTION

Figure 1:
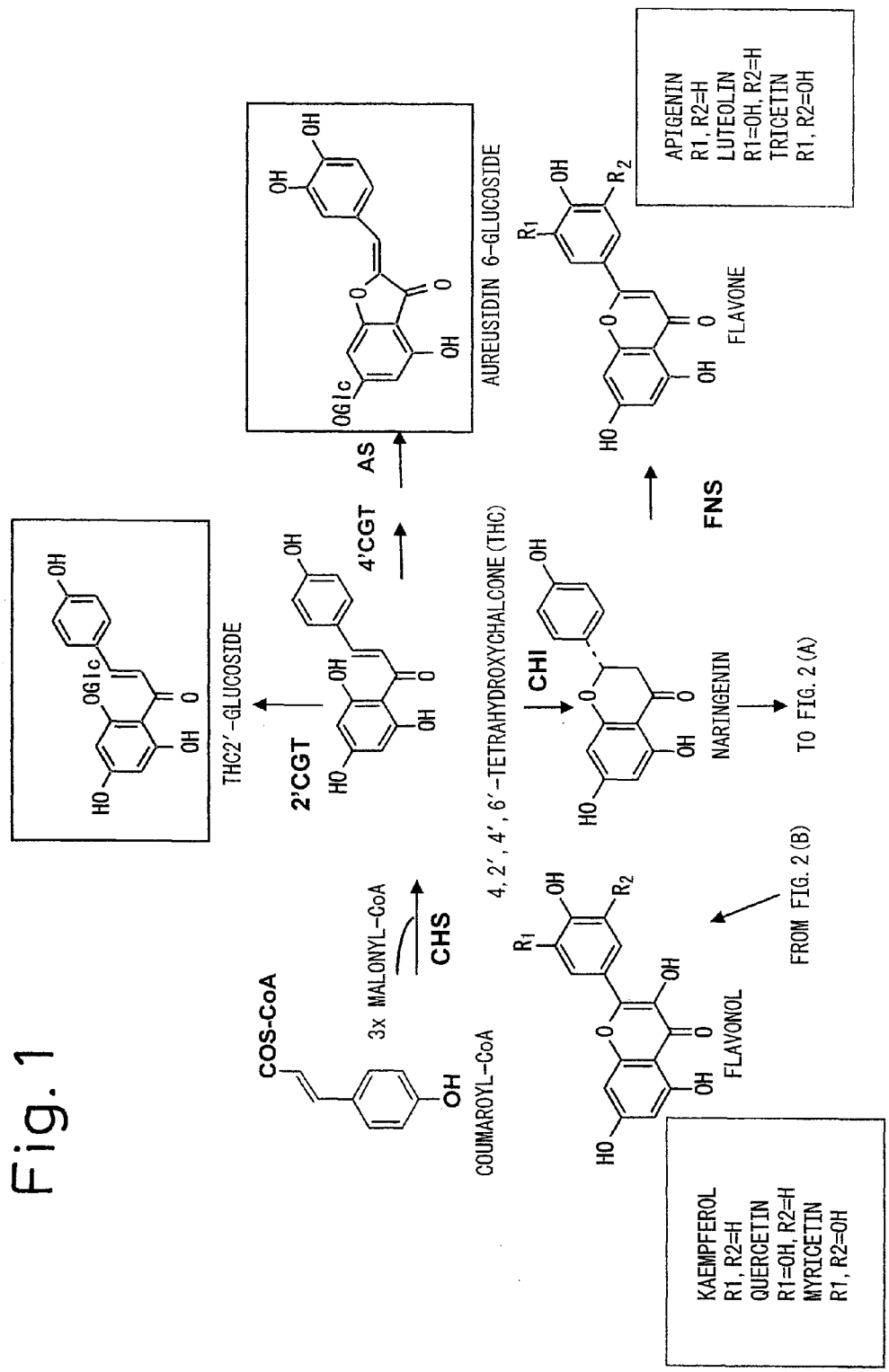
FIG. 1 shows the typical flavonoid synthesis pathway in a plant. The details of the metabolic pathway differ for different plant species, depending on the presence or absence of the enzyme genes shown. For example, yellow *Antirrhinum majus* petals have both the anthocyanin synthesis pathway and pathway that leads to aurone synthesis, whereas torenia which is a plant belonging to the family Scrophulariaceae lacks the 4'CGT and AS genes and therefore cannot synthesize aurones. The abbreviations used in the drawing are explained below. CHS=chalcone synthase; CHI=chalcone isomerase; F3H=flavanone 3-hydroxylase; DFR=dihydroflavonol 4-reductase; ANS=anthocyanidin synthase; 3GT=UDP-glucose:anthocyanidin 3-glucosylase; FLS=flavonol synthase; FNS=flavone synthase; F3'H=flavonoid 3'-hydroxylase; F3',5'H=flavonoid 3',5'-hydroxylase; 2'CGT=UDP-glucose:4,2',4',6'-tetrahydroxychalcone 2'-glucosyltransferase; 4'CGT=UDP-glucose:4,2',4',6'-tetrahydroxychalcone 4'-glucosyltransferase; AS=aureusidin synthase.

As an example of a gene according to the invention there may be mentioned one coding for the amino acid sequence listed as SEQ ID NO: 2. However, it is well known that a protein having a modified amino acid sequence with one or a plurality of amino acids added, deleted and/or substituted with other amino acids can retain the enzyme activity of the original protein. The present invention therefore also includes any protein having the amino acid sequence listed as SEQ ID NO: 2 with a modification of one or a plurality of amino acids that are added, deleted and/or substituted with other amino acids, so long as it is a protein that retains 4'CGT activity, as well as a gene coding for such a protein. Here, "a plurality" means 2-30, and preferably 2-9.

The present invention also relates to a gene that hybridizes to DNA having the nucleotide sequence listed as SEQ ID NO: 1 under the relatively mild conditions of 5×SSC, 50° C., and that codes for a protein having 4'CGT activity. Also included within the technical scope of the invention is any gene that hybridizes to DNA having the nucleotide sequence listed as SEQ ID NO: 1 under stringent conditions, and that codes for a protein having 4'CGT activity. Here, the "stringent conditions" may be, for example, 2×SSC, 65° C., but the hybridization conditions are not limited thereto because they may differ depending on the length and base composition of the DNA used as probe.

As genes selected by such hybridization there may be mentioned naturally occurring genes such as plant-derived genes, preferably Scrophulariaceae-derived genes, and more preferably *Antirrhinum majus*, *Linaria bipartita* and *Linaria japonica*-derived genes, although there is no limitation to plants. That is, the 4'CGT gene of the invention is not limited to the 4'CGT gene from *Antirrhinum majus*, *Linaria bipartita* or *Linaria japonica*, and the 4'CGT gene from other biological species that contain chalcone 4'-glucosides may be used to cultivate yellow-colored flowers. Synthetic DNA containing the 4'CGT gene may also be used in the same manner as plant-derived genes.

The gene selected by hybridization may be cDNA or genomic DNA.

As shown in the examples, a gene having homology with the conserved region of GT may be obtained by screening a cDNA library prepared from, for example, *Antirrhinum majus* or *Linaria bipartita* flower petals. DNA coding for GT having an amino acid sequence which is a modification of the amino acid sequence listed as SEQ ID NO: 2 may be synthesized by a publicly known site specific mutagenesis or PCR method using DNA having the nucleotide sequence listed as SEQ ID NO: 1. For example, a DNA fragment for amino acid sequence modification may be obtained by restriction endonuclease treatment of cDNA or genomic DNA and used as template for site specific mutagenesis or PCR using a primer corresponding to the desired modified amino acid sequence, in order to obtain a DNA fragment corresponding to the desired modified amino acid sequence. The modification-introduced DNA fragment may then be ligated to a DNA fragment coding for another portion of the enzyme of interest. Such DNA may also be chemically synthesized.

Alternatively, in order to obtain DNA coding for a protein comprising a shortened amino acid sequence, DNA coding for an amino acid sequence longer than the target amino acid sequence, for example, the full-length amino acid sequence, may be cleaved with a desired restriction endonuclease, and if the resulting DNA fragment does not code for the full-length target amino acid sequence, it may be ligated with a synthesized DNA fragment corresponding to the lacking portion of the amino acid sequence.

The GT gene obtained in this manner is expressed using a gene expression system in *E. coli* or yeast, and measurement of 4'CGT activity in the *E. coli* or yeast extract can confirm that the obtained GT gene codes for a protein exhibiting 4'CGT activity. The 4'CGT activity may be measured in the manner described in Example 3, for example, by adsorbing a chalcone serving as the substrate for 4'CGT onto a reverse-phase resin and then reacting the reverse-phase resin with extract of *E. coli* or yeast that has been transformed with the GT gene, and analyzing the produced chalcone 4'-glucoside by high performance liquid chromatography (HPLC).

The obtained 4'CGT gene may be expressed in suitable host cells to obtain 4'CGT protein as the gene product. Alternatively, an antibody for a protein or peptide having all or a portion of the amino acid sequence listed as SEQ ID NO: 2 may be used to obtain the 4'CGT gene of another organism by expression cloning.

The present invention further relates to a recombinant vector, especially an expression vector, containing the 4'CGT gene, and to host cells transformed using the vector. The host cells used may be prokaryotic or eukaryotic. As examples of prokaryotic cells there may be used publicly known host cells including bacteria belonging to the genus *Escherichia* such as *Escherichia coli*, or microorganisms belonging to the genus *Bacillus* such as *Bacillus subtilis*.

As examples of eukaryotic cells there may be used eukaryotic microorganisms, and preferably yeast or filamentous fungi. As examples of yeast there may be mentioned *Saccharomyces* yeast such as *Saccharomyces cerevisiae*, and as examples of filamentous fungi there may be mentioned *Aspergillus* microbes such as *Aspergillus oryzae* and *Aspergillus niger*, or *Penicillium* microbes. Animal or plant cells may also be used as host cells, among which mouse, hamster, monkey or human cell lines may be used as the host cells. Insect cells such as silkworm cells, or actual silkworm adults, may be used as hosts.

The expression vector of the invention includes expression regulating regions such as a promoter and terminator dependent on the host species, as well as a replication origin. As promoters for the expression vector in bacteria, and particular in *E. coli*, there may be used conventional publicly known promoters such as trc promoter, tac promoter and lac promoter. As yeast promoters there may be used, for example, glyceraldehyde 3-phosphate dehydrogenase promoter, PH05 promoter or the like and as filamentous fungi promoters there may be used, for example, amylase or trpC promoters, but there is no limitation to these promoters. As animal cell promoters there may be used viral promoters, such as SV40 early promoter or SV40 late promoter. The expression vector may be constructed by ordinary methods using restriction endonucleases, ligases and the like. Transformation of the host cells with the expression vector may also be carried out by conventional publicly known procedures.

Construction of a plant expression vector may be accomplished, for example using a binary vector such as pBI121 when using *Agrobacterium*, or using an *E. coli* vector such as pUC19 when using a particle gun. The plant cells transformed with the plant expression vector may then be selected using a marker gene such as an antibiotic resistance gene and regenerated under conditions employing a suitable plant hormone, to obtain transformed plant individuals having the 4'CGT gene introduced therein. Cultivation of the transformed plants to blooming can yield plants exhibiting the modified flower color.

The host cells transformed by the expression vector or the transformed plants may be cultured or cultivated, and the target 4'CGT protein recovered and purified from the culture, etc. by ordinary methods such as, for example, filtration, centrifugal separation, cell disruption, gel filtration chromatography, ion-exchange chromatography and the like.

The present invention is not limited only to the 4'CGT gene of *Antirrhinum majus* or *Linaria bipartita*, but may also be applied for modification of flower color by 4'CGT whether the source of the 4'CGT or 4'CGT gene is a plant, animal, microorganism or synthesized organism. The present invention relates to the use of the 4'CGT gene, and the scope of the invention encompasses plants with modified flower color by introduction and expression of the 4'CGT gene in plants, as well as their progeny, vegitatively propagated products of the foregoing and tissues of such plants, where the tissues may include cut flowers. Moreover, the scope of the present invention further encompasses plants with modified flower color by introduction and expression in plants not only of the 4'CGT gene but even AS genes other than the 4'CGT gene, and by inhibited expression of the endogenous flavonoid synthesis pathway genes of the host, as well as their progeny, vegitatively propagated products of the foregoing and tissues of such plants, where the tissues may include cut flowers.

With the current level of technology it is possible to introduce genes into plants and express those genes either constitutively or in a tissue-specific manner, or to inhibit expression of target genes by antisense, cosuppression or RNAi methods. As examples of plants to be transformed there may be mentioned rose, chrysanthemum, carnation, snapdragon, cyclamen, morning glory, begonia, impatiens, geranium, orchid, bluebell, freesia, gerbera, gladiolus, gypsophila, kalanchoe, lily, pelargonium, geranium, petunia, torenia, tulip, rice, forsythia, begonia, barley, wheat, rapeseed, potato, tomato, poplar, banana, eucalyptus, sweet potato, soybean, alfalfa, lupin, corn and cauliflower, although there is no limitation to these.

EXAMPLES

The present invention will now be explained in greater detail by the following examples. The molecular biological methods employed were based on the description in WO96/25500 or Molecular Cloning (Sambrook et al. Cold Spring Harbour Laboratory Press, 1989), unless otherwise specified.

Example 1

Construction of Yellow *Antirrhinum majus* Flower Petal cDNA Library

A cDNA library was constructed as described in the literature (Science 290, 1163 (2000)), from 5 g of fresh flower petals of the yellow *Antirrhinum majus* variety Butterfly Yellow. The obtained library consisted of $1.6 \times 10^5$ plaque forming units.

Example 2

4'CGT Gene Screening 1

Previously disclosed GT amino acid sequences were compared, and nucleotide sequences corresponding to the conserved regions of the amino acid sequences were amplified and used as probes for screening of the *Antirrhinum majus* cDNA library described in Example 1.

Five GTs were used as the probes, namely the sequences for morning glory-derived UDP-glucose:anthocyanidin 3-glucoside glucosyltransferase (3GGT) (Japanese Unexamined Patent Publication No. 2003-289884), petunia-derived 3GT (Plant Mol. Biol. 48, 401, (2002)), verbena-derived 5GT (J. Biol. Chem. 274, 7405 (1999)), *Scutellaria baicalensis*-derived GT (SBGT, Planta 210, 1006 (2000)) and gentian-derived UDP-glucose:anthocyanin 3'-glucosyltransferase (3'GT) (Plant Physiol. 132, 1652, (2003)). One oligonucleotide pair was synthesized for each GT to allow amplification of the conserved region sequence. The oligonucleotide sequences are listed as SEQ ID NO: 3-12.

```
Morning glory 3GGT
SEQ ID NO: 3:
5'-GAA ATG GTC GGA TTG GCT GGG-3'

SEQ ID NO: 4:
5'-ACC TCC ACC CCA ACT TTC AGG-3'

Petunia 3GT
SEQ ID NO: 5:
5'-GAT GCA TAA TTT GGC TAG AAA AGC-3'

SEQ ID NO: 6:
5'-CCA ATT TGC CAA ACA CTT TCC-3'

Verbena 5GT
SEQ ID NO: 7:
5'-TGC CTC GAA TGG TTG AGC ACG-3'

SEQ ID NO: 8:
5'-CTC TCA CTC TCA CAC CCG-3'

Baikal skullcap GT
SEQ ID NO: 9:
5'-CAC GAA TGC TTA GCA TGG CTC-3'
```

-continued

```
SEQ ID NO: 10:
5'-CTT ATT GCC CAC TGA AAC CCC-3'

Gentian 3'GT
SEQ ID NO: 11:
5'-TGT CTG AAT TGG CTT GAT TCC-3'

SEQ ID NO: 12:
5'-AAC CCA CAG AAA CCC CTG TTC-3'
```

The probes were labeled using a non-radioisotope DIG-nucleic acid detection system (Roche Diagnostic Corp.), with PCR under the conditions recommended by the manufacturer. Plasmids containing 1 ng of each cDNA were used as template and 100 ng of oligonucleotide specific to each gene was used as primer, for 25 cycles of PCR where each cycle consisted of reaction at 95° C. for 1 minute, 55° C. for 1 minute and 72° C. for 2 minutes. An equivolume mixture of the PCR amplification product for each gene was used as the hybridization probe for screening of the *Antirrhinum majus* cDNA library of Example 1.

The hybridization was carried out overnight at 37° C. in 5×SSC containing 30% formaldehyde, 1% SDS, and the filter was rinsed for 30 minutes at 55° C. using 5×SSC and 1% SDS. The positive signal by screening was detected using a non-radioisotope DIG-nucleic acid detection system (Roche Diagnostic Corp.), according to the method recommended by the manufacturer. Approximately 300,000 plaques were screened, leading to selection of 10 clones possessing full-length glucosyltransferase genes, which were designated as pSPB264, 1621, 1620, 1622, 1610, 1609, 1617, 1615, 660 and 658. A DNA Sequencer model 3100 (Applied Biosystems) was used to determine their cDNA sequences by the primer walking method with synthetic oligonucleotide primers. The nucleotide sequences of the amino acid-coding regions of the cDNA are listed as SEQ ID NO: 14-23.

Example 3

Assay of Chalcone GT Activity Using *E. coli*

3-1 Construction of *E. coli* Expression Vector and Expression of GT in *E. coli*

The activity of GT encoded by the ten cDNAs obtained in Example 2 was analyzed using an *E. coli* expression system. First, *E. coli* expression constructs were prepared for each cDNA. An NcoI site was introduced by PCR so as to be situated on the nucleotide sequence ATG believed to be the start codon for each cDNA, and the region from the start methionine to the end codon was linked to the NcoI and KpnI or NcoI and EcoRV sites of the *E. coli* expression vector pQE61 (QIAGEN).

The PCR solution (25 µl) for introduction of the NcoI site situated on the start methionine comprised each GT cDNA as template, 0.2 pmol/µl each of primer containing the NcoI recognition site situated on the start methionine position and primer from the 3' end to the 5' end near the stop codon, 1×ExTaq buffer (Takara), 0.2 mM dNTPs and 1.25 U ExTaq polymerase. Reaction was conducted at 94° C. for 5 minutes, followed by 28 cycles of reaction at 94° C. for 1 minute, 55° C. for 1 minute and 72° C. for 2 minutes, and then by final treatment at 72° C. for 5 minutes. The obtained PCR product was subcloned in pCR2.1 TOPO vector (INVITROGEN) according to the method recommended by the manufacturer. The DNA sequences of the amplified DNA fragments were analyzed, and after confirming lack of PCR-induced error, they were introduced into *E. coli* expression vector pQE61 (QIAGEN).

For example, for cDNA encoded in pSPB1617 (SEQ ID NO: 20), the two different primers 1617 BamHINcoI-FW (SEQ ID NO: 24) and the 1617 XhoIKpnI-RV (SEQ ID NO: 25) listed in the Sequence Listing were used for PCR, for introduction of the NcoI site lying at the start methionine position and the KpnI recognition sequence at the 3'-end of the end codon. The amplified DNA fragments were subcloned in pCR2.1 TOPO vector. After confirming lack of PCR-induced error, the DNA fragment cut out with NcoI and KpnI was linked to the NcoI and KpnI sites of pQE61, to obtain pSPB1642 as a pSPB1617 cDNA *E. coli* expression vector. Ten different GT cDNA *E. coli* expression vectors were constructed in the same manner.

```
1617BamHINcoI-FW
SEQ ID NO: 24:
5'-GGG GGA TCC ATG GCT ACT GAG AGC CAA ATA-3'

1617XhoIKpnI-RW
SEQ ID NO: 25:
5'-CCC CTC GAG GGT ACC TCA CAA AAC ATT ATT CAC
GAC-3'
```

Each expression vector was introduced into *E. coli* JM109 (TOYOBO) and pre-cultured overnight at 37° C. in LB medium containing ampicillin at a final concentration of 20 µg/ml. After adding 1 ml of pre-culturing solution to 50 µg/ml of ampicillin and 50 ml of M9 medium containing 0.5% casamino acid and culturing to A600=0.6-1.0, IPTG (Isopropyl-β-D-thiogalactopyranoside) was added to a final concentration of 0.1 mM and shake culturing was carried out overnight at 27° C., and was followed by centrifugation at 3000 rpm for 10 minutes at 4° C. to recover the cells. The cells were suspended in 10 ml of buffer solution (30 mM Tris-HCl pH 7.5, 30 mM NaCl), and after disruption of the *E. coli* with an ultrasonic treatment with a SONIFIER 250 (BRANSON), it was centrifuged at 15,000 rpm, 10 min, 4° C. and the obtained supernatant was used as the crude enzyme solution for the following activity assay.

3-2 Enzyme Activity Assay

After loading THC (500 µg/ml ethanol solution) into 1 ml of the reverse-phase resin TOYOPEARL HW-40F (TOSOH) equilibrated with $H_2O$, while diluting with $H_2O$, it was rinsed with water to obtain THC substrate fixed on the resin. To 100 µl of the resin-fixed THC there were added 200 µl of the crude enzyme solution obtained in 3-1 and 10 µl of 5 mM UDP-glucose, and reaction was conducted at 30° C. for 1 hour. After removing the supernatant by centrifugation, the precipitated resin was rinsed with water and suspended in 300 µl of 50% acetonitrile containing 0.1% TFA (Trifluoroacetic acid), and the flavonoids were freed from the resin by ultrasonic treatment. Upon centrifugation at 15,000 rpm, 5 min, 4° C., the insoluble portion of the obtained supernatant was removed with a filter (pore size: 0.45 mm, 4 mm Millex-LH, Millipore), and the supernatant was analyzed by high-performance liquid chromatography (HPLC). The analysis conditions for chalcones and their glucosides were as follows.

The column used was a Develosil C-30-UG-5 (4.5 mmφ× 150 mm, Nomura Chemical Co., Ltd.), with a mobile phase of $H_2O$ containing 0.1% TFA as solution A and 90% acetonitrile containing 0.1% TFA as solution B, and after elution for 10 minutes with a linear concentration gradient from 20% solution B to 70% solution B, it was held for 5 minutes with 70% solution B. The flow rate was 0.6 ml/min, and detection was carried out based on absorbance at 360 nm and the absorption spectrum from 250-400 nm using an SPD-M6A PDA detector (Shimadzu Corp.). Elution of THC at a retention time of 10.7 min, and 2'-glucoside and 4'-glucoside at 8.5 min under these conditions was confirmed using samples of THC and THC 2'- and 4'-glucosides.

Upon reaction of the pSPB1642-expressing *E. coli* extract, a new product in addition to the THC substrate was detected, eluting at 8.5 min. Since these were not detected with reaction using crude extract prepared in the same manner from *E. coli* expressing only pQE61 vector or boiled crude extract of *E. coli* expressing pSPB1642, it was concluded that the product was produced by GT expressed from pSPB1642. The structure of the product was also examined by $^1$H-NMR analysis. The analysis was performed using a JNM-EX400 (JEOL), under conditions as described in the literature (Plant Physiology 132, 1652 (2003)). As a result, the THC glucoside produced by the expression product of pSPB1642 was demonstrated to be THC 2'-glucoside. Thus, it was concluded that the cDNA expressed by pSPB1642, i.e. pSPB1617 cDNA, codes for a protein with 2'CGT activity.

Example 4

4'CGT Gene Screening 2

The approximately 300,000 clones of the yellow *Antirrhinum majus* flower petal cDNA library were re-screened using the full-length pSPB1617 cDNA as the probe. The probe labeling by PCR was conducted in the same manner as described in Example 2, using 1617-F (SEQ ID NO: 26) and 1617-R (SEQ ID NO: 27) primers. The screening and nucleotide sequence analysis methods were also the same as in Example 2.

```
1617-F
SEQ ID NO: 26:
5'-ATG GGA GAA GAA TAC AAG AAA ACA-3'

1617-R
SEQ ID NO: 27:
5'-TAA AAT TTG GTA GTT AAA CCG ATG TA-3'
```

As a result, five novel GT genes were obtained: pSPB1721, 1724, 1723, 1719 and 1725. The respective sequences are listed in the Sequence Listing (SEQ ID NO: 28-31 and 1).

Among these, pSPB1725 cDNA contained a 1374 by translation region (excluding the stop codon) coding for a 50.8 kDa molecular weight protein composed of 457 amino acids, with an isoelectric point of 6.82. The amino acid sequence (SEQ ID NO: 2) encoded by the pSPB1725 cDNA was compared with the previously reported GT amino acid sequence, and only showed 14% homology with Livingstone Daisy GT (Plant J. 19, 509 (1999)), 18% homology with perilla 5GT, 18% homology with perilla 3GT, 23% homology with gentian 3'GT and 31% homology with the amino acid sequence of the protein encoded by pSPB1617 used as the probe. The software used for homology analysis was ClustalW included with MacVector ver. 6.5.3 (Oxford Molecule), with parameters of Matrix Blosum 30, ketuple: 1, Gap penalty: 3, Top-diagonals: 5, Windows Size: 5.

Example 5

Expression of Obtained cDNA in *E. coli*

5-1. Expression Vector Construction

The five cDNAs obtained in Example 4 were examined by assaying the enzyme activity of the protein encoded by each cDNA using an *E. coli* expression system. The expression vector construction and expression method and activity assay method were the same as in Example 3. For pSPB1725, for example, PCR reaction was conducted using the following two primers 1725-NcoI (SEQ ID NO: 32) and 1725-KpnI (SEQ ID NO: 33) for introduction of the NcoI recognition sequence at the 5'-end of the start codon.

```
1725-NcoI
SEQ ID NO: 32:
5'-CCC ATG GGA GAA GAA TAC AAG AAA-3'

1725-KpnI
SEQ ID NO: 33:
5'-GGT ACC TAT AAA ATT TGG TAG TTA AA-3'
```

The PCR solution (25 µl) consisted of 10 ng pSP1725 DNA, 1×ExTaq buffer (Takara), 0.2 mM dNTPs, 0.2 pmol/µl each of the 1725-NcoI and 1725-KpnI primers and 1.25 U ExTaq polymerase.

Reaction was conducted at 94° C. for 5 minutes, followed by 28 cycles of reaction at 94° C. for 1 minute, 55° C. for 1 minute and 72° C. for 2 minutes, and then by final treatment at 72° C. for 7 minutes. The obtained PCR product was subcloned in pCR2.1 TOPO vector (INVITROGEN) according to the method recommended by the manufacturer. Upon confirming the nucleotide sequence of the amplification product, the approximately 1.4 kb fragment cut out from pCR2.1 TOPO vector by NcoI and KpnI treatment was linked to the NcoI and KpnI sites of pQE61 (QIAGEN) to obtain the *E. coli* expression vector pSPB1768. This was then introduced into *E. coli* JM109 (TOYOBO). *E. coli* expression vectors were also constructed for the other four cDNAs in the same manner using pQE61, and were introduced into JM109.

5-2 Recombinant Protein Expression in *E. coli* and GT Activity Assay

The *E. coli* transformants obtained in Example 5-1 were cultured under the same conditions as Example 3 and used for activity assay of the proteins encoded by each cDNA. As a result, a peak attributed to THC glucoside was detected in the reaction product between THC and the crude enzyme solution of pSPB1768-containing *E. coli*. In order to identify the THC glucoside in greater detail, HPLC analysis was again performed under conditions for separation of THC 2'-glucoside and THC 4'-glucoside, as follows.

The column used was a YMC-ODS-A312 (6 mmϕ×150 mm, YMC Corp.), and with a mobile phase of $H_2O$ containing 2% acetic acid as solution A and methanol as solution B, for elution for 15 minutes with a linear concentration gradient from 15% solution B to 40% solution B and holding for 5 minutes with 40% solution B, followed by elution for 10 minutes with a linear concentration gradient from 40% solution B to 62% solution B and holding for 2 minutes with 62% solution B. The flow rate was 1.0 ml/min. Detection was carried out based on absorbance at 360 nm and the absorption spectrum from 250-400 nm using an SPD-M6A PDA detector (Shimadzu Corp.).

Under these conditions, THC elutes at a retention time of 26.7 min, THC 2'-glucoside elutes at 19.8 min and 4'-glucoside elutes at 20.6 min. The THC glucoside found in the pSPB1768-expressing *E. coli* extract and THC reaction solution was believed to be 4'-glucoside because it eluted at 20.6 min by analysis under these conditions. Since it was not detected upon reaction of crude extract prepared in the same manner from *E. coli* expressing only pQE61 vector, it was presumably the product of GT encoded by pSPB1725. These results confirmed that GT encoded by pSPB1725 cDNA exhibits activity of transferring glucose to the 4'-hydroxyl group of THC.

A new peak for elution at 15.5 min was also detected in addition to THC 4'-glucoside in the reaction solution. This substance exhibited the absorption spectrum of naringenin, and matched the retention time for a naringenin 7-glucoside standard. Thus, the product that eluted at 15.5 min was believed to be naringenin 7-glucoside produced by post-glucosylation ring closure of THC 4'-glucoside produced by 4'CGT encoded in pSPB1725, or naringenin 7-glucoside produced by the action of 4'CGT on naringenin produced by ring closure of THC.

Example 6

Expression Analysis of 4'CGT Gene in *Antirrhinum majus* Flower Petals

The expression profile of the 4'CGT gene encoded by pSPB1725 in yellow *Antirrhinum majus* flower petals was analyzed by RT-PCR. Flower petals of yellow *Antirrhinum majus* (Butterfly Yellow variety) which accumulate aurones were separated at 5 growth stages. The five stages are, in order of youth, stages 1 (budding petal length of $\leq 1$ cm), 2 (budding petal length of 1.0-1.5 cm), 3 (budding petal length of 1.5-2.0 cm), 4 (petal length of 2.0-2.5 cm, just prior to blooming) and 5 (petal length of $\geq 2.5$ cm, bloomed petals), where stage 5 corresponds to the mature flower petal.

The RNA was extracted from 1 g of separated flower petals, using an RNeasy Plant Mini Kit (QIAGEN). Reverse transcription reaction was conducted using 1 μg of obtained RNA as template to obtain cDNA. A SuperScript First-Strand Synthesis System for RT-PCR (GIBCO BRL) was used for the cDNA synthesis, and the synthesis conditions were according to the conditions recommended by the system manufacturer. PCR was performed using the cDNA obtained at each stage as template and the 1725-NcoI (SEQ ID NO: 32) and 1725-KpnI (SEQ ID NO: 33) described in Example 5 as primers. For comparison between 4'CGT gene expression and endogenous gene expression, the *Antirrhinum majus* glyceraldehyde-3-phosphate dehydrogenase (GAPDH) gene (SEQ ID NO: 34) (Nature 339, 46 (1989)) was used as the internal standard gene, and primers AmGAPDH-F (SEQ ID NO: 35) and AmGAPDH-R (SEQ ID NO: 36) were synthesized for amplification of this gene. Also, primers AmAS-F (SEQ ID NO: 37) and AmAS-R (SEQ ID NO: 38) were synthesized for amplification of the *Antirrhinum majus* AS gene, as a comparison gene.

```
AmGAPDH-F
SEQ ID NO: 35:
5'-TGT TGC TGT TAA CGA TCC AT-3'

AmGAPDH-R
SEQ ID NO: 36:
5'-AGC TCT TCC ACC TCT CCA-3'

AmAS-F
SEQ ID NO: 37:
5'-ATG TTC AAA AAT CCT AAT ATC CGC-3'
```

-continued

```
AmAS-R
SEQ ID NO: 38:
5'-TTA GCC ATC AAG CTC AAT CTT GAC A-3'
```

The PCR conditions were 12 cycles of 94° C. for 1 minute, 55° C. for 1 minute and 72° C. for 2 minutes, with the same reaction composition as in Example 3. The PCR product was separated by 1% agarose gel electrophoresis, and then blotted on a Hybond-N nylon membrane (Amersham) according to ordinary protocol for detection of amplification product by hybridization. The hybridization method employed the previously mentioned non-radioisotope DIG-nucleic acid detection system, DIG DNA labeling and detection kit, and was carried out according to the method recommended by the manufacturer. The probes used were cDNA for 4'CGT encoded in *Antirrhinum majus* AS, GAPDH and pSPB1725, and DIG labeling was accomplished using primers specific for each gene (SEQ ID NO: 32, 33, 35-38) in the same manner as Example 2.

As a result, both the 4'CGT and AS genes reached expression peaks at stage 4, thus exhibiting similar expression patterns with time. The expression patterns for both genes also did not appear inconsistent with the accumulation patterns for chalcone 4'-glucosides and aurones in yellow *Antirrhinum majus* flower petals (Plant Sci. 160, 229 (2001)).

These results suggest that expression of the 4'CGT gene encoded in pSPB1725 is under the same control as the AS gene in *Antirrhinum majus* flower petals, and that both are involved in the same synthesis pathway, namely the synthesis pathway of aurone.

Example 7

Co-Expression of 4'CGT and AS in Plant 7-1 Construction of 4'CGT Expression Cassette Plasmid pBE2113-GUS (Plant Cell Physiol. 37, 49 (1996)) was digested with SnaBI and religated to remove the omega sequence, and the obtained plasmid was designated as pUE6. Separately, plasmid pUCAP (van Engelen et al. Transgenic Research 4, 288-290, 1995) was digested with Asci and the ends blunted, after which Pad linker was inserted to prepare a plasmid designated as pUCPP. A fragment of pUE6 from the El$_2$35S promoter to the NOS terminator was inserted at the HindIII and EcoRI sites of pUCPP to obtain plasmid pSPB540. The GUS gene portion of pSPB540 was replaced with the 4'CGT cDNA fragment cut out from pSPB 1725, and the obtained plasmid was designated as pSFL 203. That is, pSFL2O3 comprises pUCPP as the vector and has the 4'CGT expression cassette controlled by El$_2$35S promoter and NOS terminator.

7-2 Construction of AS Expression Cassette

*Antirrhinum majus*-derived AS cDNA (Science 290, 1163, (2000)) was inserted at the EcoRI and XhoI sites of pBluescript II SK-vector (Stratagene) to obtain a plasmid designated as pSPB251. An AS expression construct having the MacI promoter, the AS cDNA fragment cut out from pSPB251 and the MAS terminator linked in plasmid pBIN-PLUS (van Engelen et al. Transgenic Research 4, 288-290, 1995) was designated as pSPB1624.

7-3 Creation of 4'CGT and AS Co-Expression Construct

The pSFL203 of 7-1 was cleaved with PacI and the chalcone glucosylating enzyme gene expression cassette was cut out and inserted at the PacI site of plasmid pSPB1624 from 7-2. The obtained construct was designated as pSFL201.

Thus, pSFL201 is designed so as to constitutively express the 4'CGT and AS genes when introduced into plant cells.

Example 8

Co-Expression of 4'CGT and AS and Inhibition of Torenia DFR in Plants 8-1 Construction of Torenia-Derived DFR Gene Expression-Inhibiting Cassette The cDNA for torenia dihydroflavonol reductase (DFR) was obtained in the manner described in the literature (Plant Science 153, 33, 2000). The torenia DFR cDNA was linked with the vector pBluescriptII SK– to obtain a plasmid designated as pTDF10. This was used as a template for PCR in the manner described in Example 3, using M13 reverse primer (SEQ ID NO: 39) from the vector sequence and the primer ThDFR-NcoI (SEQ ID NO: 40) having an NcoI recognition site introduced therein by nucleotide substitution in the torenia DFR cDNA sequence. The approximately 0.75 kb fragment that was obtained was cloned in pCR2.1-TOPO (Invitrogen), and after confirming the nucleotide sequence, the 0.75 kb torenia DFR cDNA sequence was cut out with SacI and NcoI.

Also, plasmid pTDF10 was cleaved with BamHI and NcoI, and a fragment containing 1.1 kb was recovered from the 5' end of torenia DFR cDNA. Separately, plasmid pUCAP described in 7-1 was digested with PacI and its ends blunted, after which an AscI linker was inserted to obtain a plasmid designated as pUCAA. A fragment including El$_2$35S promoter-GUS-NOS terminator cut out from pUE6 was inserted at the HindIII and EcoRI sites of pUCAA, and the obtained plasmid was designated as pSPB541. Plasmid pSPB541 was cleaved with BamHI and SacI, the GUS gene portion was removed, and there were inserted therein the 0.75 kb fragment and 1.1 kb fragment from torenia DFR cDNA, ligated in a direction linking the NcoI sites of both fragments. Plasmid pSFL314 obtained in this manner, when introduced into a plant, can transcribe double-stranded RNA from the torenia DFR cDNA sequence under the control of El$_2$35S promoter, thus inhibiting expression of the torenia DFR gene by RNAi.

```
M13 reverse primer
SEQ ID NO: 39:    5'-AACAGCTATGACCATG-3'

ThDFR-NcoI
SEQ ID NO: 40:    5'-GCTTTACCATGGAGTAATGAGCTT-3'
```

8-2 Co-Expression of 4'CGT and AS and Creation of Construct for Inhibition of Torenia DFR Gene Expression An XhoI linker was inserted upstream of the NOS terminator of pUE6 described in 7-1. The plasmid was digested with BamHI and XhoI to obtain a fragment comprising the El$_2$35S promoter-vector-NOS terminator, and this fragment was ligated with the AS cDNA fragment cut out from pSPB215 with BamHI and XhoI as described in 7-2 to obtain plasmid pSPB211. The AS expression cassette was cut out from pSPB211 with HindIII and EcoRI and inserted at the HindIII and EcoRI sites of pBINPLUS. The 4'CGT expression cassette obtained by PacI cleavage of pSFL203 described in 7-1 was inserted at the PacI site of the plasmid obtained in this manner, to obtain plasmid pSFL304 having the 4'CGT and AS expression cassettes linked in tandem. Also, the torenia DFR double-stranded RNA transcription cassette described in 8-1 was inserted at the AscI site of pSFL304 to obtain plasmid pSFL307. That is, pSFL307 includes three cassettes, for 4'CGT and AS expression and torenia DFR gene expression inhibition.

Example 9

Co-Expression of 4'CGT and AS and Inhibition of Torenia F3H Gene Expression in Plant 9-1 Cloning of Torenia F3H cDNA and Construction of Expression Inhibition Cassette for the Gene F3H cDNA obtained from perilla (Plant Mol Biol., 35, 915 (1997)) was used as a probe to obtain cDNA coding for the same enzyme in torenia. Specifically, a torenia cDNA library (Molecular Breeding, 6, 239, 2000) of approximately 200,000 phage was screened in the same manner as Example 2 to obtain the torenia F3H cDNA listed as SEQ ID NO: 41. The torenia F3H cDNA was linked with the vector pBluescriptII SK– to obtain a plasmid designated as pSPB266. This was used as template for PCR in the manner as Example 3, using M13 reverse primer (SEQ ID NO: 39) from the vector sequence and the primer ThF3H-SalI-1 (SEQ ID NO: 42) having a SalI recognition site inserted therein by nucleotide substitution in the torenia F3H cDNA sequence.

The approximately 0.9 kb fragment that was obtained was cloned in pCR2.1-TOPO (Invitrogen), and the nucleotide sequence was confirmed. In the same manner, the primer ThF3H-SalI-2 (SEQ ID NO: 43) having a SalI recognition site inserted therein by nucleotide substitution in the torenia F3H cDNA sequence and M13 reverse primer were used to prepare an approximately 0.75 kb DNA fragment which was cloned in pCR2.1-TOPO, and the nucleotide sequence was confirmed. Plasmid pSPB541 described in Example 8-1 was cleaved with BamHI and SacI, the GUS gene portion was removed, and there were inserted therein a 0.9 kb fragment cut out from pCR2.1-TOPO by cleavage with BamHI and SalI and a 0.7 kb fragment cut out from pCR2.1-TOPO by cleavage with SacI and SalI, ligated in a direction linking the SalI sites of both fragments. Plasmid pSFL313 obtained in this manner, when introduced into a plant, transcribes double-stranded RNA derived from the torenia F3H cDNA sequence under the control of El$_2$35S promoter, thus inhibiting expression of the torenia F3H gene by RNAi.

```
ThF3H-SalI-1
SEQ ID NO: 42:    5'-TTCTCTGTCGACGCCCATTGCC-3'

ThF3H-SalI-2
SEQ ID NO: 43:    5'-CGCCGTGTCGACTCGCTTGAAG-3'
```

9-2 Co-Expression of 4'CGT and AS and Creation of Construct for Inhibition of Torenia F3H Gene Expression The torenia F3H RNAi cassette was cut out from the pSFL313 described in 9-1 by cleavage with AscI and inserted at the AscI site of pSFL304 described in Example 8-2 to obtain plasmid pSFL308. That is, pSFL308 includes three cassettes, for 4'CGT and AS expression and torenia F3H gene expression inhibition.

Example 10

Gene Expression and Flower Color Analysis in Plant

Plasmids pSFL201, pSFL307 and pSFL308 described in Example 7-9 were introduced into torenia (variety Summerwave Blue (Suntory Flowers Ltd.)) by a publicly known method. The transformation method was based on the method described in Mol. Breeding. 6, 239, (2000). Individuals exhibiting selection marker resistance were selected out and their flower colors observed. Among the pSFL201-introduced varieties, 22 of the 35 transformant lines exhibited altered flower color with respect to the host, displaying a yellowish blue or yellowish gray color.

However, no pure yellow color was found. Among the pSFL307-introduced varieties, 19 of the 36 transformant lines exhibited altered flower color with respect to the host. Also, 6 of the 19 lines with altered flower color displayed almost pure yellow flower colors virtually without any tint of the original blue color of the host. Among the pSFL308-introduced varieties, 24 of the 39 transformant lines exhibited altered flower color with respect to the host. Also, 17 of the 24 lines with altered flower color displayed almost pure yellow flower colors virtually without any tint of the original blue color of the host.

Pigment analysis was performed on the lines with relatively notable flower color alteration.

The flower petals of the host variety and the transformants were immersed with 50% acetonitrile containing 0.1% trifluoroacetic acid (TFA) for extraction of the flavonoids, and then the aureusidin 6-glucosides and anthocyanidins were analyzed by high performance liquid chromatography (HPLC). For anthocyanidin analysis, the flavonoids extracted from the flower petals were dissolved in 6N HCl and hydrolyzed by holding in boiling water for 20 minutes, after which the flavonoids were re-extracted with amyl alcohol and supplied for analysis. The HPLC conditions were as follows.

First, detection of AU 6-glucoside was performed using a SHIM-PACK FC-ODS column (50×4.6 mm, Shimadzu Corp.), and for the reverse phase, $H_2O$ containing 0.05% TFA was used as solution A and acetonitrile containing 0.05% TFA was used as solution B. Elution for 3 minutes with a linear concentration gradient from 10%-23% solution B was followed by 17 minutes with 23% solution B, and then elution for 2 minutes with a linear concentration gradient from 23%-80% solution B was followed by 3 minutes with 80% solution B. Elution was then performed for 2 minutes with a concentration gradient from 80%-10% solution B. The flow rate was 0.8 ml/min. Detection was carried out based on absorbance at 360, 400 nm and the absorption spectrum from 250-500 nm using an SPD-M10AVP PDA detector (Shimadzu Corp.). Under these conditions, THC 4'-glucoside and AU 6-glucoside samples elute at retention times of 14.17 min and 6.19 min, respectively.

The column used for anthocyanidins was a YMC-ODS-A A312 (6×150 mm, YMC Corp.). For the reverse phase there was used a mixture of acetic acid, methanol and $H_2O$ at 60:70:270, maintained for 11 minutes. Detection was carried out based on absorbance at 520 nm and the absorption spectrum from 400-600 nm using an SPD-M10AVP PDA detector (Shimadzu Corp.). Under these conditions, malvidin elutes at a retention time of 9.12 min.

As a result, with the pSFL201-introduced transformants, products matching the retention times and absorption spectra of THC 4'-glucoside and AU 6-glucoside were confirmed to be produced in the flower petals at 0.02% and 0.05% respectively (W/W as fresh flower petal weight). Because anthocyanidins native to the host were also present in the transformants, it may be assumed that the yellowish blue or gray colors observed in the transformants were due to the copresence of anthocyanidins such as malvidin with the THC 4'-glucoside and AU 6-glucoside.

On the other hand, with the pSFL307- and 308-introduced transformants, products matching only the retention times and absorption spectra of the aurone AU 6-glucoside were confirmed to be produced in the flower petals at 0.09% (W/W as fresh flower petal weight) in both cases. In the pSFL307- or pSFL308-introduced lines, it was confirmed that anthocyanidins native to the host were notably reduced to 10-50% of those anthocyanidins in the host flower petals.

Example 11

Confirmation of 4'CGT Gene Introduction by Genomic Southern Hybridization

Lines among the transformants obtained in Example 10 which had relatively large accumulation of THC 4'-glucoside and AU 6-glucoside based on the flower petal pigment analysis were selected (3 lines from each construct-introduced variety) and subjected to genomic hybridization. A Phytopure Plant DNA Extraction kit (Amersham) was used for extraction of genomic DNA from approximately 1 g of transformant leaves, according to the method recommended by the manufacturer. Twenty μg of the obtained genomic DNA was cleaved with restriction endonuclease KpnI, and after separation by 0.7% agarose gel electrophoresis and transfer to a Hybond-N+ nylon membrane according to ordinary protocols, a non-radioisotope DIG-nucleic acid detection system was used for hybridization.

Figure 2:
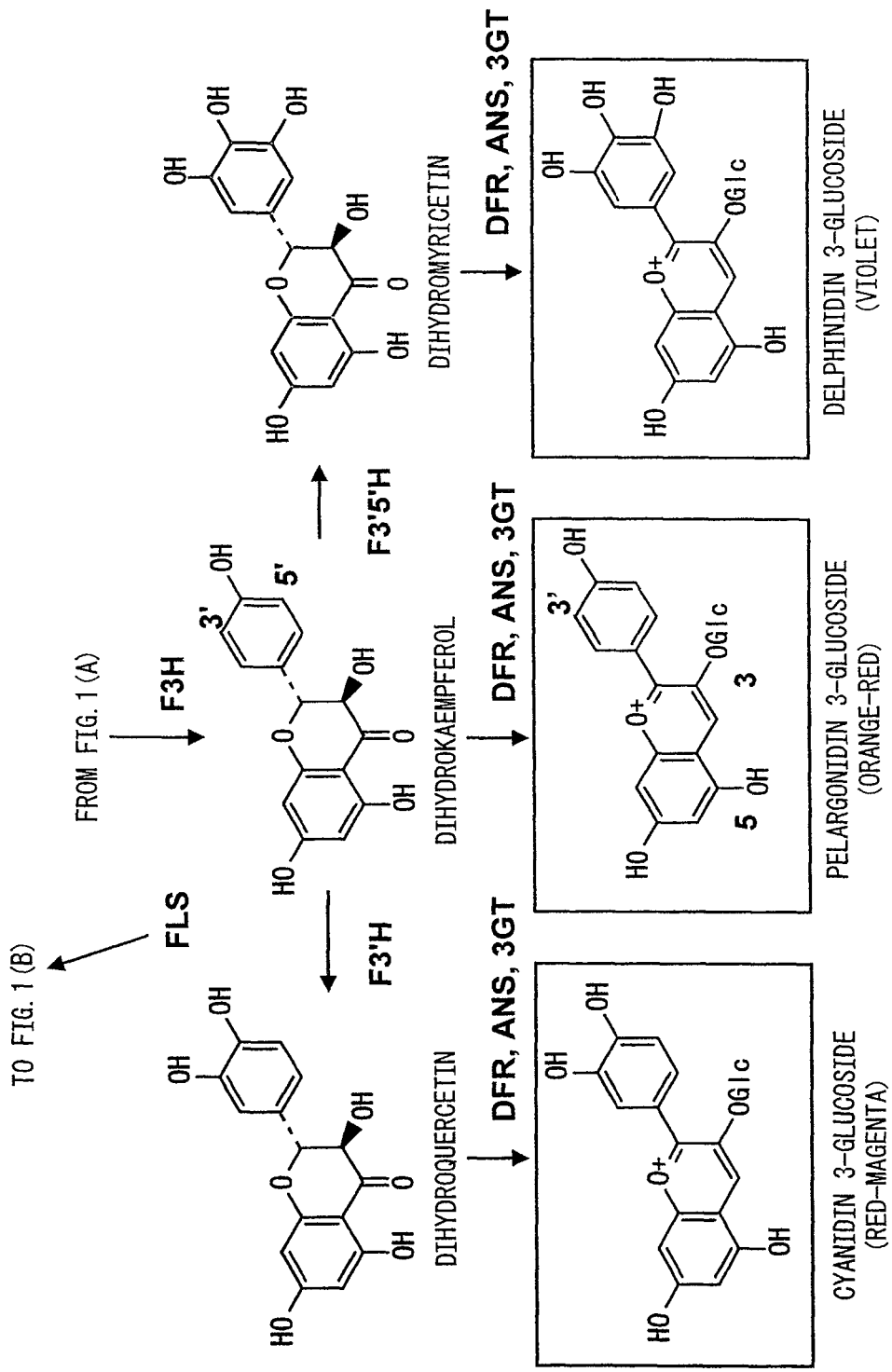
FIG. 2 is a continuation of FIG. 1.
Figure 3:
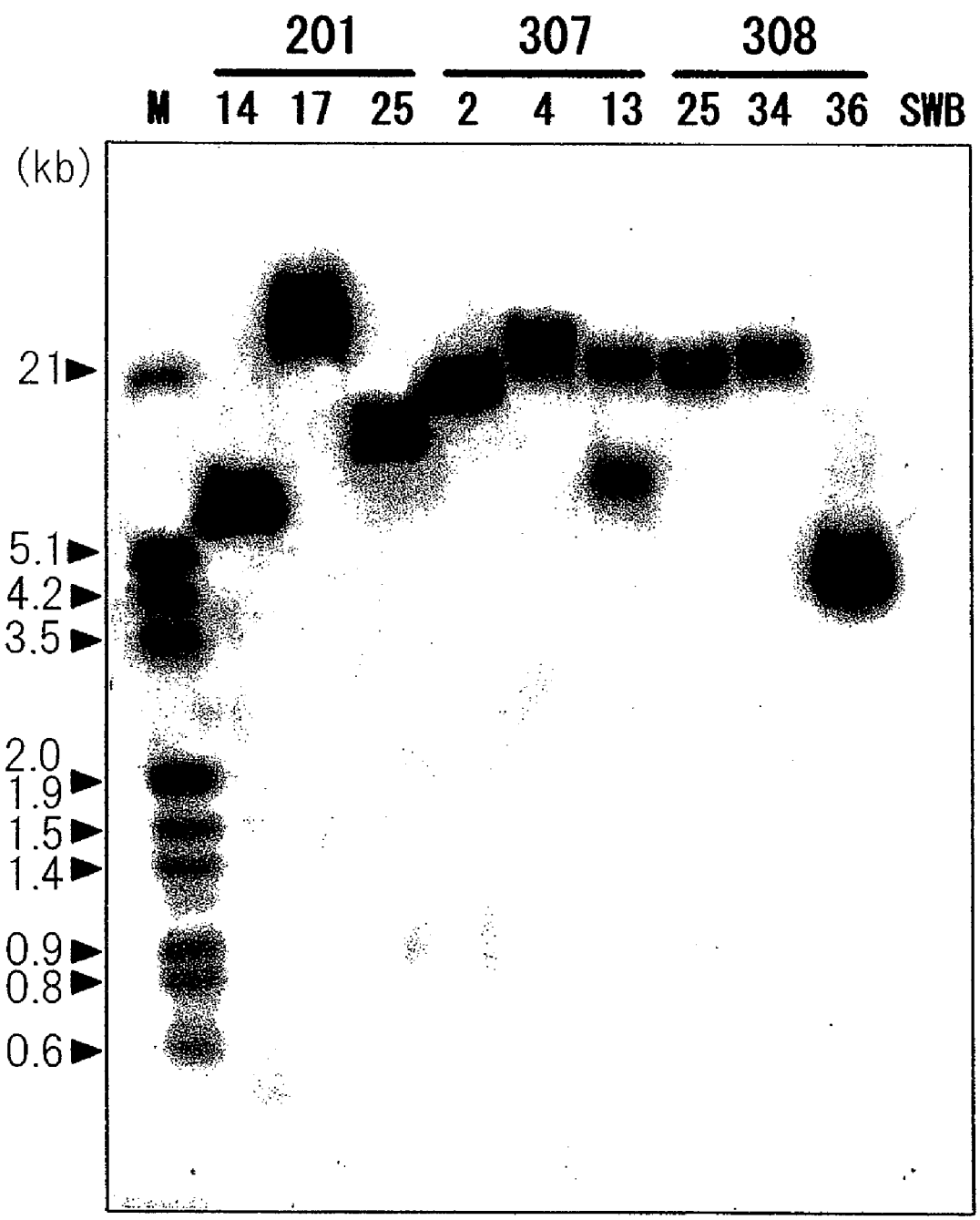
FIG. 3 shows the results of Southern hybridization of a torenia transformant. Genomic DNA was extracted from pSFL201, pSFL307 and pSFL308 introduced torenia leaves (variety Summerwave Blue) transformants, and after KpnI cleavage, was subjected to Southern hybridization using the 4'CGT gene as the probe. The numerals at the top of each lane indicate the lineage numbers of the transgenic constructs and transformants. SWB represents Summerwave Blue used as the host. M1 and M2 are DIG-labeled size markers (Roche), and the size of each band is shown at left.

The methods of DIG labeling, hybridization and detection of the 4'CGT gene probes were according to the methods recommended by the manufacturer, as in Example 6. The hybridization results are shown in FIG. 2. Judging from restriction enzyme maps for pSFL201, pSFL307 and pSFL308, it is possible to estimate the number of 4'CGT gene copies introduced into each transformant based on the number of bands detected by genomic Southern hybridization.

As one band was observed for all of the pSFL201-introduced lines, it is deduced that each has one copy of the introduced gene. Individuals of line Nos. 2 and 4 among the pSFL307-introduced lines had 1 copy, while individuals of line No. 13 exhibited 2 bands and therefore presumably have introduced 2 copies of 4'CGT cDNA. Since one band was observed for all of the pSFL308-introduced lines, it is deduced that each has one copy of the introduced gene.

Example 12

Introduced Gene Expression Analysis by Quantitative RT-PCR

An RNeasy Plant Mini Kit (QIAGEN) was used for extraction of total RNA from buds of the stock variety and each of the transformant lines, cDNA was synthesized from 1 μg of the obtained total RNA using a SuperScript™ First-Strand Synthesis System for RT-PCR (Invitrogen). Using 1 μl of the obtained cDNA as template, expression of torenia DFR and F3H and transcription products of the exogenous genes AS and 4'CGT was quantitatively analyzed with an ABI PRISM 7000 Sequence Detection System (Applied Biosystems). Using the manufacturer's recommended software "Primer Express", there were designed oligoprimers for specific amplification of each gene, and specific hybridizing TaqMan probes fluorescently labeled at both ends, and these were used for reaction. Quantitation of expression was carried out using the oligoprimers of SEQ ID NO: 54 and 55 and the TaqMan probe of SEQ ID NO: 56 for torenia DFR, the oligoprimers of SEQ ID NO: 57 and 58 and the TaqMan probe of SEQ ID NO: 59 for torenia F3H, the oligoprimers of SEQ ID NO: 60 and 61 and the TaqMan probe of SEQ ID NO: 62 for AS and the oligoprimers of SEQ ID NO: 63 and 64 and the TaqMan probe of SEQ ID NO: 65 for 4'CGT.

```
Torenia DFR
SWB DFR-1158F
                                              (SEQ ID NO: 54)
5'-AAT GGG ATG CTT CCG ACT TCT-3'

SWB DFR-1223R
                                              (SEQ ID NO: 55)
5'-CAG TGG TTT CTG CCA TTG CTT-3'

SWB DFR-1180T
                                              (SEQ ID NO: 56)
5'-AGG AAA AAA CAG GCT GAA AA-3'

Torenia F3H
Torenia F3H-1035F
                                              (SEQ ID NO: 57)
5'-CAT CGA GCG GTG GTG AAT T-3'

Torenia F3H-1101R
                                              (SEQ ID NO: 58)
5'-CTG GCG ATG GGT TTT GAA A-3'

Torenia F3H-1055T
                                              (SEQ ID NO: 59)
5'-AAA CAC GAA TAG AAT GTC G-3'

AS
AmAS-1545F
                                              (SEQ ID NO: 60)
5'-GAA GAT GAC CTT GCG GTG ATT T-3'

AmAS-1638R
                                              (SEQ ID NO: 61)
5'-TTG TCC TCT TCC CCT TTA TAG GTT T-3'

AmAS-1582T
                                              (SEQ ID NO: 62)
5'-AGT TCG CCG GGA GTT TCG TGA GTC TG-3'

4'CGT
AmGTcg12-908F
                                              (SEQ ID NO: 63)
5'-GGT TGG CCC GCA TTT CA-3'

AmGTcg12-966R
                                              (SEQ ID NO: 64)
5'-TAG AAA ACC CTC CGG CAG AA-3'

AmGTcg12-929T
                                              (SEQ ID NO: 65)
5'-AGA TGG ACT TAA ATG CG-3'
```

As an endogenous control there was used torenia glyceraldehyde phosphate dehydrogenase (GAPDH). The oligoprimers used were SWB GAPDH-794F (5'-GCA TTG AGC AAG ACG TTT GTG-3') (SEQ ID NO: 66) and SWB GAPDH-859R (5'-ACG GGA ACT GTA ACC CCA TTC-3') (SEQ ID NO: 67), and the TaqMan probe used was SWB GAPDH-816T (5'-AGC TTG TGT CGT GGT ACG-3') (SEQ ID NO: 68).

The reaction solution was prepared to a total volume of 50 μl, comprising the cDNA of each transformant line, 1×TaqMan Universal Master Mix (Applied Biosystems), 100 nM of each oligoprimer and 100 nM of TaqMan probe. Reaction was conducted at 50° C. for 2 minutes and 95° C. for 10 minutes, followed by 40 cycles of reaction at 95° C. for 15 seconds, 60° C. for 1 minute, and the production of PCR amplification product was detected in real time. As a result, high expression was confirmed both for introduced AS and 4'CGT in the pSFL201-introduced lines. It was also confirmed that the introduced AS and 4'CGT were both expressed in the pSFL307-introduced lines, and that endogenous DFR mRNA was inhibited to about 10% compared to the stock variety. In the pSFL308-introduced lines, it was confirmed that both the introduced AS and 4'CGT were expressed, while endogenous F3H mRNA was inhibited to about 5% compared to the stock variety.

Example 13

Assay of 4'CGT Glucosylating Activity on PHC

PHC 4'-glucoside has been confirmed in yellow *Antirrhinum majus* flower petals (Sato, T., et al. Plant Sci. 160, 229-236 (2001)), and it is known that AS can produce bracteatin and bracteatin 6-glucoside using PHC and PHC 4'-glucoside as substrate. In order to determine whether or not 4'CGT can catalyze PHC 4'-position glucosylation reaction, the glucosylating activity of 4'CGT for PHC was assayed. Enzyme reaction was conducted according to Example 5-2, using recombinant 4'CGT expressed in *E. coli* and PHC fixed on resin by the same method as Example 3-2 as substrate. The HPLC conditions were as follows.

The column used was a YMC-ODS-A312 (6 mmφ×150 mm, YMC Corp.), with a mobile phase of $H_2O$ containing 2% acetic acid as solution A and methanol as solution B, for elution for 22 minutes with a linear concentration gradient from 15% solution B to 40% solution B and holding for 5 minutes with 40% solution B, followed by elution for 14 minutes with a linear concentration gradient from 40% solution B to 62% solution B and holding for 2 minutes with 62% solution B. The flow rate was 1.0 ml/min. Detection was carried out based on absorbance at 360 nm and the absorption spectrum from 220-400 nm using an SPD-M10AP PDA detector (Shimadzu Corp.). Under these conditions, THC elutes at a retention time of 38.2 min, THC 2'-glucoside elutes at 27.7 min, 4'-glucoside elutes at 30.0 min, PHC elutes at 32.4 min and PHC 4'-glucoside elutes at 24.3 min. The PHC glucoside found in the pSPB1768-expressing *E. coli* extract was identified as PHC 4'-glucoside because it eluted at 24.3 min by analysis under these conditions. When PHC was reacted with a crude extract prepared in the same manner from *E. coli* expressing only pQE61 vector, no PHC glucoside was detected. Thus, PHC 4'-glucoside is presumably a product of GT encoded in pSPB1725. These results confirmed that GT encoded in pSPB1725 cDNA exhibits activity of transferring glucose to the 4'-hydroxyl group of PHC. The results described above demonstrated that 4'CGT catalyzes not only 4'-glucosylation of THC but also 4'-glucosylation of PHC.

Example 14

Functional Analysis of 4'CGT and AS Using Torenia Transformants 14-1 Creation of Construct A 2.4 kb 4'CGT expression cassette portion was cut out from the pSFL203 described in Example 7 with PacI, and was inserted at the PacI site of pBINPLUS to obtain plasmid pSFL209. Plasmid pSFL209 expresses 4'CGT alone in plants.

A 2.7 kb F3H expression cassette was cut out from pSFL313 described in Example 9 with AscI, and this was inserted at the AscI site of pBINPLUS to obtain plasmid pSFL210. Plasmid pSFL210 is designed to transcribe double-stranded RNA of the torenia F3H gene in torenia plants, thereby inhibiting expression of F3H.

Separately, for AS, an AS cDNA fragment cut out from pSPB251 described in Example 7 with BamHI and XhoI was inserted at the BamHI and XhoI sites of pSPB120' described in a patent application (P2003-293121), to obtain vector pSPB211 which expresses AS in plants.

14-2 RT-PCR Expression Analysis of Introduced Genes and Flower Color Analysis

Plasmids pSFL209, pSFL210 and pSFL211 described in Example 14-1 were introduced into torenia (variety Summerwave Blue (Suntory Flowers Ltd.)) by the method described in Example 10. The transformation method was based on the method described in Mol. Breeding. 6, 239, (2000). Individuals exhibiting selection marker resistance were selected out. An RNeasy Plant Mini Kit (QIAGEN) was used for extraction of total RNA from buds of each line of the transformants and the stock variety Summerwave Blue, and cDNA was synthesized from 1 μg of the obtained total RNA by reverse transcription using a SuperScript™ First-Strand Synthesis System for RT-PCR (Invitrogen). RT-PCR reaction was also conducted using ExTaq (TaKaRa) according to the method recommended by the manufacturer. For amplification of AS mRNA there were used primers AmAS-INSITU-FW (5'-AATTATTTCCCAATGTTCAAAAAT-3') (SEQ ID NO: 44) and AmAS-INSITU-RV (5'-TGGAGCTTTAGGTTTGT-GAAA-3') (SEQ ID NO: 45), for amplification of *Antirrhinum majus* 4'CGT mRNA there were used primers KIR-INSITU-FW (5'-ATGGGAGAAGAATACAAGAAAAC-3') (SEQ ID NO: 46) and KIR-INSITU-RV (5'-TCTTAC-GATAAAACAAACTCA-3') (SEQ ID NO: 47), for amplification of endogenous F3H mRNA there were used primers T.F3H-923F (5'-ATC ATC GAG CGG TGG TGA A-3') (SEQ ID NO: 48) and T.F3H-1339R (5'-TGG CCG ACT AGG CAA TAC AAT-3') (SEQ ID NO: 49), and for amplification of mRNA of GAPDH as the endogenous standard gene there were used primers T.GAPDH-F87 (5'-CCC TTC TGT TTG GTG AAA AGC C-3') (SEQ ID NO: 50) and T.GAPDH-R692 (5'-CCT CGG ATT CCT OCT TGA TAG C-3') (SEQ ID NO: 51). As a result, of the 41 transformant lines obtained among the pSFL209-introduced lines, the introduced *Antirrhinum majus* 4'CGT transcripts were detectable in 37 lines, but no flower color alteration was observed in any of the lines. Of the 44 transformant lines obtained among the pSFL210-introduced lines, significant decrease in the amount of endogenous F3'H transcript was detectable in 37 lines, and these lines exhibited white or mixed violet/white flower colors. In addition, of the 41 transformant lines obtained among the pSPB211-introduced lines, expression of the introduced AS was confirmed in 31 lines, and no flower color alteration was observed in any of the lines.

Pigment analysis was carried out for the pSFL209-introduced lines and pSPB211-introduced lines in which transcripts of the introduced genes were detected, and for the pSFL210-introduced lines that exhibited white flower color. The flower petals of Summerwave Blue and each of the transformants were wetted with 50% acetonitrile containing 0.1% trifluoroacetic acid (TFA) for extraction of the flavonoids, and then AU6-glucoside and anthocyanidins were analyzed by high performance liquid chromatography (HPLC). Analysis of the anthocyanidins was carried out in the same manner as Example 10. The HPLC conditions were as follows.

First, detection of AU6-glucoside was performed using a SHIM-PACK FC-ODS column (50×4.6 mm, Shimadzu Corp.), and for the reverse phase, H₂O containing 0.05% TFA was used as solution A and acetonitrile containing 0.05% TFA was used as solution B. Elution for 3 minutes with a linear concentration gradient from 10%-23% solution B was followed by 17 minutes with 23% solution B, and then elution for 2 minutes with a linear concentration gradient from 23%-80% solution B was followed by 3 minutes with 80% solution B. Elution was then performed for 2 minutes with a concentration gradient from 80%-10% solution B. The flow rate was 0.8 ml/min. Detection was carried out based on absorbance at 360 and 400 nm and the absorption spectrum from 250-500 nm using an SPD-M10AVP PDA detector (Shimadzu Corp.). Under these conditions, THC 4'-glucoside and AU6-glucoside samples elute at retention times of 14.17 min and 6.19 min, respectively. The column used for anthocyanidins was a YMC-ODS-A A312 (6×150 mm, YMC Corp.). For the reverse phase there was used a mixture of acetic acid, methanol and H₂O at 60:70:270, maintained for 11 minutes. Detection was carried out based on absorbance at 520 nm and the absorption spectrum from 400-600 nm using an SPD-M10AVP PDA detector (Shimadzu Corp.). Under these conditions, malvidin elutes at a retention time of 9.12 min.

As a result, with the pSFL209-introduced lines, a product matching the retention time and absorption spectrum of THC 4'-glucoside was confirmed to be produced at 0.036-0.762 mg per gram of fresh flower petal weight. Anthocyanidins naturally found in the host were also present.

The anthocyanidin levels in the pSFL210-introduced lines were reduced to about 1% of the anthocyanidin level in host flower petals.

In the pSPB211-introduced lines, no alteration in flavonoid pigment was observed compared to the host. No product matching the retention times and absorption spectra of aurones was detected in any of the transformants.

This indicated that chalcone glucosides and aurones are not synthesized in plants merely by inhibition of F3H expression and overexpression of AS, but that aurones are synthesized by co-expression of 4'CGT and AS. Overexpression of 4'CGT alone can accumulate chalcone 4'-glucoside, for alteration in flower color.

Example 15

Cloning of 4'CGT cDNA from *Linaria bipartita*

In the same manner as Example 1, RNA extracted from *Linaria bipartita* buds and bloomed flower petals was used to prepare a cDNA library. A library of 8.0×10⁵ pfu/ml was obtained from the bud-obtained RNA, while a cDNA library of 1.0×10⁶ pfu/ml was obtained using bloomed flower petal cDNA.

Screening was performed using approximately 3.0×10⁵ pfu of phage from each library, with 4'CGT cDNA encoded in the *Antirrhinum majus* pSPB1725 described in Example 4 as the probe. The probe labeling, hybridization and subsequent membrane rinsing and detection were carried out in the same manner as Example 2. Nineteen positive clones were finally obtained as a result. When nucleotide sequencing was performed on 8 of the cDNAs having lengths (about 1.5 kb) as expected for cDNA encoding chalcone glucosyltransferase, the 8 clones all had identical sequences and the clone with the longest cDNA was designated as pSFL409. The nucleotide sequence of this cDNA is listed as SEQ ID NO: 69, and the amino acid sequence encoded by it is listed as SEQ ID NO: 70. The amino acid sequence encoded by the pSFL409 cDNA was shown to have high homology with that of *Antirrhinum majus* chalcone 4'-glucosyltransferase. In comparison with *Antirrhinum majus* chalcone 4'-glucosyltransferase cDNA, however, the amino acid sequence encoded by pSFL409 cDNA was found to be incomplete cDNA lacking about 10 by from the start methionine. Therefore, a Gene Racer RACE kit (Invitrogen) was used for amplification of the upstream cDNA fragment including the putative start methionine by the 5'RACE method, and this was cloned in pCRII-TOPO vector and designated as plasmid pSFL417. *Linaria bipartita* cDNA including the full length showed 65% sequence identity with *Antirrhinum majus* 4'-glucosyltransferase on the amino acid level.

Example 16

Expression and Activity Assay of *Linaria bipartita* cDNA in *E. coli*

The full-length *Linaria bipartita* cDNA was introduced at the NcoI and KpnI sites of the *E. coli* expression vector pQE61, and activity of the protein encoded by this *Linaria bipartita* cDNA was analyzed with an *E. coli* expression system. First, for creation of the *E. coli* expression construct, PCR was carried out using pSFL417 as template and primers 417-NcoI (CCCATATATAGCCATGGAAGATACCATCG) (SEQ ID NO: 52) and 409-EcoRI (TAGTGTTGTG-GAGTCGGGGGATTTCG) (SEQ ID NO: 53). Thus, an NcoI site was inserted at the start methionine position of pSFL417, and an EcoRI site was inserted at the 3'-end. The products of cleaving this with NcoI/EcoRI and cleaving pSFL409 cDNA with EcoRI/KpnI were cloned at the NcoI/KpnI site of the *E. coli* expression vector pQE61, to obtain an *E. coli* expression construct (pSFL418) comprising the full-length *Linaria bipartita* cDNA.

This was introduced into *E. coli* JM109 and the recombinant protein activity was assayed in the same manner as Example 12. Upon reaction of the pSFL418-possessing *E. coli* extract using THC as substrate, THC 4'-glucoside was detected with a retention time of 30.0 min. In separate reaction of pQE61-possessing *E. coli* extract with THC as a control experiment, absolutely no THC 4'-glucoside was detected. Glucosylation activity for PHC was also assayed in the same manner as Example 12. As a result, upon reaction of pSFL418-possessing *E. coli* extract, PHC 4'-glucoside was detected with a retention time of 24.3 min. However, no PHC glucoside was detected in the control experiment. These results suggest that *Linaria bipartita* cDNA cloned in SFL418 codes for 4'CGT.

The invention claimed is:

1. An isolated gene coding for a protein having the activity of transferring a sugar to the chalcone 4'-position, wherein the protein having the activity of transferring a sugar to the chalcone 4'-position has the amino acid sequence of SEQ ID NO: 70.

2. The gene according to claim 1, which is derived from the family *Scrophulariaceae*.

3. The gene according to claim 2, which is derived from *Antirrhinum majus* or *Linaria bipartita*.

4. A vector comprising the gene according to claim 1.

5. An isolated host cell transformed by the vector according to claim 4.

6. A plant having the gene according to claim 1 introduced therein or a progeny of said plant having the same properties as said plant, wherein the progeny comprises the gene according to claim 1, or a vegetatively propagated plant or tissue from the plant or plant progeny.

7. Flowers cut from the plant or plant progeny according to claim 6.

8. A method for transferring a sugar to the chalcone 4'-position comprising expressing the gene according to claim 1.

9. A plant having modified flower color obtained by introducing and expressing the gene according to claim 1 into a plant, or a progeny of said plant having the same properties as said plant, wherein the plant progeny comprises the gene according to claim 1.

10. The plant or plant progeny according to claim 9, wherein the flower color has a yellow tint.

11. A method for altering flower color to yellow in a plant comprising introducing and expressing the gene according to claim 1 together with a gene coding for *Antirrhinum majus* aureusidin synthase in a plant to alter the flower color to yellow.

* * * * *